United States Patent [19]

Chiou

[11] Patent Number: 5,283,236
[45] Date of Patent: Feb. 1, 1994

[54] SYSTEMIC DELIVERY OF POLYPEPTIDES THROUGH THE EYE

[75] Inventor: George C. Y. Chiou, College Station, Tex.

[73] Assignee: Orbon Corporation, Palo Alto, Calif.

[21] Appl. No.: 966,706

[22] Filed: Oct. 26, 1992

Related U.S. Application Data

[60] Division of Ser. No. 412,979, Sep. 26, 1989, Pat. No. 5,182,258, which is a continuation-in-part of Ser. No. 326,200, Mar. 20, 1989, abandoned.

[51] Int. Cl.$^5$ .................... A61K 37/26; A61K 37/64; A61K 47/00
[52] U.S. Cl. .......................................... 514/2; 514/3; 514/12
[58] Field of Search ................................ 514/3, 12, 2

[56] References Cited

U.S. PATENT DOCUMENTS

| | | | |
|---|---|---|---|
| 4,093,709 | 6/1978 | Choi et al. | 424/19 |
| 4,186,184 | 1/1980 | Zaffaroni | 424/14 |
| 5,182,258 | 1/1993 | Chiou | 514/3 |

FOREIGN PATENT DOCUMENTS

0115727A1  6/1984  European Pat. Off.
87/03473   6/1987  PCT Int'l Appl.

OTHER PUBLICATIONS

Galloway, J. A., et al., "Factors influencing the Absorption, Serum Insulin Concentration, and Blood Glucose Responses After Injections of Regular Insulin and Various Insulin Mixtures", *Diabetes Care* (1981) 4(3):366-376.

Monkhouse, D.C., et al., "The Effect of EDTA on the Resistance of Pseudomonas Aeruginosa to Benzalkonium Chloride", *Aust. J. Pharm.* (1967) 48(570):S70-S75.

Moses, A. C., "Routes of Administration: Nasal", *Proceedings of Land O'Lake* (1986) 86, Merrimac, WI, Lecture Note, pp. 1 10.

Mygind, N., et al, "Aerosol Distribution in the Nose", *Rhinology* (1978) vol. XVI, pp. 79-88.

Bito, L. Z., et al., "Transport of Prostaglandins Across the Blood-Brian and Blood Aqueous Barriers and the Physiological Significance of these Absorptive Transport Processes", *Exp. Eye Research Suppl.* (1977) pp. 229-243.

McClure, D. A., "The Effect of a Pro-Drug of Epinephrine (Dipivalyl Epinephrine) in Glaucoma—General Pharmacology, Toxicology, and Clinical Experience", in *Pro-Drugs as Novel Drug Delivery Systems, ACS Symposium Series No. 14*, Higuchi, T., et al., editors (published by American Chemical Society, Washington, D.C., 1975), pp.; 224-235.

Lee, V. H. L., et al., "Metabolic and Permeation Barriers to the Ocular Absorption of Topically Applied Enkephalins in Albino Rabbits", *J. Ocular Pharmacol.* (1986) 2(4):345-352.

Christie, C. D., et al., "Insulin Absorption by the Conjunctival Membranes in Rabbits", *J. Clin. Invest.* (1931) 10:787-793.

Ueno, N., et al., "Ocular Pharmacology of Drug Release Devices", in *Controlled Drug Delivery, Vol II, Clinical Applications*, Bruck, S. D., editor, (published by CRC Press, Inc., Florida, 1983), Chapter 4, pp. 89-109.

Chiou, G. C. Y., et al., "Treatment of Hypoglycemia (List continued on next page.)

*Primary Examiner*—Michael G. Wityshyn
*Assistant Examiner*—Choon Koh
*Attorney, Agent, or Firm*—Morrison & Foerster

[57] ABSTRACT

Compositions and methods for systemic delivery of polypeptides through the eyes are disclosed. The compositions include a systemically active polypeptide at a concentration such that the composition is substantially isotonic with tear fluid. The compositions may include a permeation-enhancing agent to aid systemic absorption of higher molecular weight polypeptides, as well as peptidase inhibitors. Therapeutically effective amounts of the polypeptide compositions can be administered to the eyes where the drug passes into the nasolacrimal duct and becomes absorbed into circulation.

4 Claims, 16 Drawing Sheets

OTHER PUBLICATIONS with Glucagon Eye Drops", *J. Ocular Pharmacol.* (1988) 4(2):179-186.

Chiou, G. C. Y., et al., "Systemic Delivery of Enkephalin Peptide Through Eyes", *Life Sciences* (1988) 43(6):509-514.

Chiou, G. C. Y., et al., "Reduction of Blood Glucose Concentration with Insulin Eye Drops", *Diabetes Care* (1988) 11(9):750-751.

Chiou, G. C. Y., et al., "Systemic Delivery of Polypeptides with Molecular Weights of Between 300 and 3500 Through the Eyes", *Journal of Ocular Pharmacology* (1988) 4(2):165-177.

Chiou, G. C. Y., et al., "Systemic Delivery of Insulin Through Eyes to Lower the Glucose Concentration", *J. Ocular Pharmacol.* (1989) 5(1):81-91.

Saettone, M. F., et al., "Vehicle Effects in Opthalmic Bioavailablity: An Evaluation of Polymeric Inserts Containing Pilocarpine", *J. Pharm. Pharamcol.* (1984) 36:229-234.

Aungst, B. J., et al., "Site Dependences of Absorption--Promoting Actions of Laureth 9, Na Salicylate, $Na_2EDTA$, and Aprotinin on Rectal, Nasal, and Buccal Insulin Delivery", *Pharmaceutical Research* (1988) 5(5):305-308.

Lee Pharm. Technology (Apr. 1987) pp. 28-38.

Lee Pharmacy International (Jun. 1985) pp. 135-138.

Hirai et al Int'l Journal of Pharmaceutics 9 (1981) 173-184.

SYSTEMIC DELIVERY OF POLYPEPTIDES THROUGH THE EYE

CROSS-REFERENCE TO RELATED APPLICATIONS

This application is a division of application Ser. No. 07/412,979 filed Sep. 26, 1989, now U.S. Pat. No. 5,182,258, which is a continuation-in-part application of Ser. No. 07/326,200, filed Nov. 20, 1989, now abandoned.

TECHNICAL FIELD

The present invention relates generally to the administration of therapeutic drugs and more particularly to the systemic delivery of polypeptides through the eyes.

BACKGROUND OF THE INVENTION

Therapeutic drugs have traditionally been administered orally or by injection. However, several pharmaceuticals now being developed are not easily administered via these methods. For example, many drugs, particularly peptides, are degraded by digestive enzymes and/or the acidity present in the gastrointestinal tract and cannot be taken orally. Additionally, many substances are not readily absorbed in the gastrointestinal tract due to the low permeability of the intestinal membrane to hydrophilic compounds. Thus, these drugs must be administered parenterally.

Injections, however, can be painful and must be given under sterile conditions to prevent the spread of AIDS and other infectious diseases. Furthermore, substances, such as insulin, administered subcataneously, show marked individual variability with respect to absorption See, e.g., Galloway, J. A., et al., *Diabetes Care* (1981) 4:366-376. Additionally, repeated injections, often necessary to control such chronic diseases as diabetes mellitus, can cause undesirable side effects such as scar-ring, irritation and localized edema. Therefore, patients often fail to comply with the strict regimen required to adequately treat such disorders, thus resulting in further medical complications. For instance, diabetic cataracts and retinopathy can occur in diabetics who fail to comply with a prescribed treatment plan.

Furthermore, several disorders are not amenable to self-help using injectables, although this is the most desirable method of treatment. For example, hypoglycemic crisis is preferably treated with intravenous, intramuscular or subcutaneous injections of glucagon or intravenous injection of glucose solutions. Patients experiencing a hypoglycemic episode cannot easily treat themselves with injections as their motor functions are impaired. However, treatment is crucial since prolonged hypoglycemia can lead to irreversible coma. Generally, patients must resort to eating sugar candies, dextrose tablets or paste in order to raise the blood glucose concentration. This method is less than desirable since the substances must travel to the intestine for absorption and timing is crucial in such a crisis.

Drugs have also been delivered intranasally via nasal drops, sprays and/or inhalers. However, the amount of drug that reaches the nasal mucosa and ultimately becomes absorbed into the systemic circulation can be less than optimal. Experimenters have used permeation-enhancing agents to aid absorption through the nasal mucosa. See, e.g., Hirai, S., et al., *Intl. J. Pharmaceutics* (1981) 9:173-184; Monkhouse, D. C., and Groves, G. A., *Aust. J. Pharm.* (1967) 48:S70-S75; Moses, A. C., Proceedings of Land O'Lake, (1986) 86, Merrimac, WI, Lecture Note, p. 6.

It is difficult, however, to achieve consistent drug distribution using these methods and delivery of a constant dose of drug intranasally is problematic. Medical practitioners have attempted to use a metered-dose mechanical spray pump in an effort to achieve constant delivery. However, drugs so delivered have been found to be unevenly distributed in the septal wall with little being found in the lateral wall. Mygind, N., et al., *Rhinology* (1978) XVI: 79-88.

Other modes of administration include buccal, vaginal, rectal, dermal and tracheal delivery, none of which have been enthusiastically adopted due to societal resistance and inconvenience.

The eye has several unique anatomical characteristics. It is protected physically by tough layers of blood-ocular barriers. Bito, L. Z., et al., *The Ocular and Cerebrospinal Fluids*, Academic Press, 1977, pp. 229-243. The cornea is composed of an aqueous phase, the stroma, sandwiched by two lipid layers, the epithelium and endothelium, respectively. Most biological systems possess the opposite orientation. The nasolacrimal duct drains tears and other substances from the eye and is lined with absorptive mucosa. Thus, substances delivered into the ocular cul-de-sac can enter the systemic circulation via the nasolacrimal system without significantly entering the eyes.

Drugs administered into the eye are generally intended for disorders of the eye itself and are not given to alleviate other systemic pathologies. However, much of the drug so administered is not absorbed by the eye, for reasons discussed above, and enters the systemic circulation via the nasolacrimal system. Often, the concentrations required to provide desired ophthalmic effects can result in undesirable drug loads for the systemic circulation and sometimes toxic side-effects. For example, epinephrine has been used to treat eye disorders however, the majority of instilled epinephrine enters the systemic circulation as a result of absorption through the nasolacrimal drainage system and has been reported to produce systemic alpha- and beta-adrenergic side effects. McClure, D. A., General Pharmacology, Toxicology, and Clinical Experience, ACS Symposium Series, *The American Chemical Society* (1975), Number 14. Thus, the use of eye drops to deliver ophthalmic drugs has been problematic.

Attempts to deliver other drugs through the eye have been made but have generally been ineffective. For example, corneal absorption of enkephalins in rabbits has been studied, and it was found that close to 100% of the enkephalins recovered in the corneal epithelium were in hydrolyzed form due to peptidase cleavage thereof. Lee, V. H. L., et al., *J. Ocular Pharmacol.* (1986) 2:345.

Insulin was delivered to the rabbit conjunctiva with variable effects. Christie, C. D., and Hanzal, R. F., *J. Clin. Invest.* (1931) 10:787. Furthermore, the rabbit eye is proportionately larger than the human eye when compared to body size. Thus, enough drug can be administered to the rabbit eye to elicit a systemic response. The human eye, on the other hand, being very small in comparison to the body, generally cannot accommodate the volume required in order to elicit an adequate response. Furthermore, when very concentrated drug solutions are administered to the eye to avoid the use of large volumes, the ocular tonicity is disrupted causing discomfort and eye irritation. For reviews of other systems and mechanisms of ocular drug delivery see Lee, V. H. L., Pharmaceutical Technology Apr. 1987:26 and Lee, V. H. L., Pharmacy International (1985) 6:135.

Drugs can be administered to the eye using a variety of methods. For example, controlled-release formulations have been used to deliver ophthalmic drugs to the eye for the treatment of eye diseases and infections. Such formulations include matrix-type drug delivery systems such as hydrophilic soft contact lenses, soluble ocular inserts and scleral buckling materials. Capsule-type drug delivery systems, such as the device Ocusert ®, have been used for the delivery of the antiglaucoma agent, pilocarpine, to the eye. Implantable silicone rubber devices have been used in the treatment of intraocular malignancies. For a review of these sustained-release systems, see Ueno, N., et al., "Ocular Pharmacology of Drug Release Devices," in *Controlled Drug Delivery*, Stephen D. Bruck, ed., vol. II, chap. 4, CRC Press, Inc. (1983).

SUMMARY OF THE INVENTION

The present invention is based on the discovery that a wide range of polypeptides can be delivered efficiently via the eye to produce sustained drug concentrations in the systemic circulation. This method of administration is simple, convenient and painless. Furthermore, the blood concentrations of substances so administered are often sustained for longer periods of time when compared to intravenous administration of a therapeutic dose of the same drug. Additionally, the dose of a polypeptide drug delivered via the eye can be readily controlled since the amount of formulation passing into the nasolacrimal duct is relatively constant. The subject invention can also be used to deliver polypeptide drugs directly to the eye to treat disorders therein.

In one embodiment, the present invention is directed to a pharmaceutical composition for systemic delivery by ocular administration and absorption in the nasolacrimal duct. The composition includes a systemically active polypeptide in a pharmaceutically acceptable vehicle, the polypeptide in the composition being present at a concentration such that the composition is substantially isotonic with tear fluid. A permeation enhancing agent is also present to enhance nasolacrimal absorption of the polypeptide into the systemic circulation.

Another embodiment of the present invention is directed to a pharmaceutical composition for systemic delivery by ocular administration and absorption in the nasolacrimal duct. The composition includes a systemically active polypeptide in an ocular delivery device. The ocular delivery device is formulated to release the polypeptide into tear fluid at a rate such that the concentration of polypeptide in the tear fluid does not significantly disrupt the tonicity of tear fluid.

In still another embodiment of the subject invention, a method is provided for delivering a polypeptide drug systemically comprising administering a therapeutically effective concentration of the drug formulated in a pharmaceutically acceptable vehicle into the eye, the concentration being less than the amount that will cause significant ocular hypertonicity. An effective amount of a permeation-enhancing agent is coadministered with the drug, whereby the drug passes into the nasolacrimal duct where it is readily absorbed into systemic circulation.

Another embodiment of the present invention provides a method for delivering a polypeptide drug systemically comprising administering a therapeutically effective amount of the drug in an ocular delivery device The device is formulated to release the polypeptide drug into tear fluid at a rate such that the concentration of polypeptide in the tear fluid does not significantly disrupt the tonicity of the tear fluid The released drug passes into the nasolacrimal duct where it is absorbed into systemic circulation.

Further embodiments of the instant invention will readily occur to those of ordinary skill in the art.

DETAILED DESCRIPTION

Figure 1:
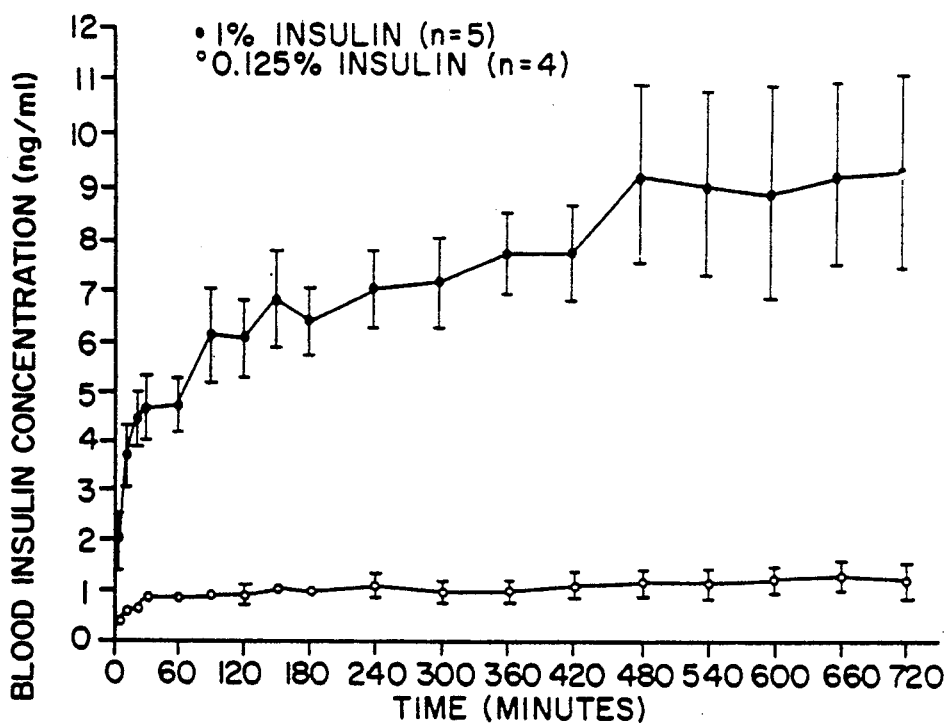
FIG. 1 depicts the absorption of insulin solutions into systemic circulation via the eyes. Each point is a mean of 4 and 5 values for 0.125% and 1.0% insulin concentrations, respectively. The bars represent the standard error of the mean ("SEM").

In describing the present invention, the following terms will be employed, and are intended to be defined as indicated below.

A "systemically active polypeptide" is one that is delivered via the circulation to act at a site remote from its entry into the body. Additionally, such a polypeptide should retain its biological activity for an effective period of time when present in the circulatory system of the subject to which it is administered. The polypeptide can be recombinantly-derived, purified, or present in compositions of the subject invention in crude form.

The terms "polypeptide" and/or "polypeptide drug" are used in their broadest sense, i.e., any polymer of amino acids (dipeptide or greater) linked through peptide bonds. Thus, the terms include proteins, oligopeptides, protein fragments, analogs, muteins, fusion proteins and the like. These terms also encompass amino acid polymers as described above that include additional moieties. Thus, the terms "polypeptide" and "polypeptide drug" include glycoproteins, lipoproteins, phosphoproteins, metalloproteins, nucleoproteins, as well as other conjugated proteins.

A "permeation-enhancing agent" is an agent that increases the amount of nasolacrimal absorption into systemic circulation of a substance coadministered therewith. Representative enhancers include surfactants, including cationic, anionic and nonionic detergents, bile salts and acids, chelating agents, fusidic acid derivatives, among others. Such agents are discussed more fully below.

A "peptidase inhibitor" is a substance that substantially inhibits the enzymatic activity of peptidases.

A composition of the present invention is "substantially isotonic with tear fluid" when it has substantially the same osmotic pressure as that found in the tear fluid. Generally, a solution with a tonicity equal to that of a 0.9% sodium chloride solution is isotonic. However, solutions equivalent in tonicity to a range of 0.5% to 1.8% sodium chloride will also be tolerated by the eye and will find use with the present invention.

By "hypertonicity" is meant that state where the osmolality of the subject fluid is increased above that found in the isotonic state. "Significant" hypertonicity refers to a hypertonic state that would damage the anatomical constituents of the eye and/or surrounding tissue. Generally, solutions with a tonicity greater than a 1.8% sodium chloride solution would be considered "significantly hypertonic."

The term "therapeutically effective amount" as used herein refers to the amount of polypeptide drug sufficient to elicit at least a desired threshold response to the drug in a subject to which the drug is administered. The precise amount will vary with the particular polypeptide drug employed, the age and condition of the subject treated, and the nature and severity of the condition. However, therapeutically effective amounts of many drugs are known or can be readily determined by one of skill in the art.

An "effective amount" of a permeation-enhancing agent is an amount that will increase nasolacrimal absorption of a coadministered drug so that blood levels of the drug can reach a concentration required to elicit a threshold response thereto without significantly disrupting the isotonicity of the tear fluid.

The blood concentration of a polypeptide drug administered according to the present invention is dependent on (1) the concentration of drug delivered and (2) the amount of drug absorbed via the conjunctiva and nasolacrimal system. Higher molecular weight polypeptides are not as readily absorbed as smaller polypeptides. Thus, a larger amount of the higher molecular weight polypeptide must be administered in order to achieve adequate blood concentrations. However, the delivery of a polypeptide in an amount greater than about 10% (w/v) generally results in a significantly hypertonic solution, not suitable for insertion into the eye. A permeation enhancer as described above can be used to increase absorption of higher molecular weight polypeptides so that the amount of drug delivered will not significantly disturb the isotonic environment of the eye. The amount of enhancer used should not be so much as to cause eye irritation. An effective amount of enhancer will vary depending on the enhancing agent used, however, concentrations on the order of 0.1%–2% (w/v) will find use with the present invention.

A "pharmaceutical composition", according to the present invention, is one that includes a polypeptide drug. The composition may also contain a pharmaceutically acceptable vehicle. The vehicle should be compatible with the active ingredient of the pharmaceutical composition. Suitable vehicles for ocular use are, for example, sterile isotonic solutions such as isotonic sodium chloride or boric acid solutions. These vehicles typically contain sodium chloride or boric acid, respectively, as well as benzalkonium chloride and sterile distilled or purified water. Also useful is phosphate buffered saline (PBS), pH 7.4. Other suitable vehicular constituents include phenylmercuric nitrate, sodium sulfate, sodium sulfite, sodium phosphate and monosodium phosphate.

The compositions may also contain auxiliary substances i.e. antimicrobial agents such as chlorobutanol, parabans or organic mercurial compounds; pH adjusting agents such as sodium hydroxide, hydrochloric acid or sulfuric acid; and viscosity increasing agents such as methylcellulose. One of ordinary skill in the art will easily find substitutions for the above auxiliary substances. The final composition should be sterile, essentially free of foreign particles, and have a pH that allows for optimum drug stability. Generally pH values in the range of 5-8 will find use with the subject compositions. Preferably, the pH will be as close to the pH of tear fluid, i.e., 7.4, as possible.

Typically, the compositions of the subject invention are prepared as solutions, suspensions, ointments, gels, or ocular delivery devices such as drug-impregnated solid carriers that are inserted into the eye. If such a carrier is used, the above-mentioned vehicles are unnecessary. A variety of polymers can be used to formulate ophthalmic drug carriers. Saettone, M. F., et al., *J. Pharm. Pharmacol.* (1984) 36:229, and Park, K., et al., in *Recent Advances in Drug Delivery Systems*, James M. Anderson and sung Wan Kiy, eds, Plenum press (1984), pp. 163-183, describe such polymers, the disclosures of which are incorporated herein by reference in their entirety. Drug release is generally effected via dissolution or bioerosion of the polymer, osmosis, or combinations thereof. The device should be formulated to release the polypeptide at a rate that does not significantly disrupt the tonicity of tear fluid.

More specifically, several matrix-type delivery systems can be used with the subject invention. These systems are described in detail in Ueno, N., et al., supra, the disclosure of which is incorporated herein by reference in its entirety. Such systems include hydrophilic soft contact lenses impregnated or soaked with the desired drug, as well as biodegradable or soluble devices that need not be removed after placement in the eye. These soluble ocular inserts can be composed of any degradable substance that can be tolerated by the eye and that is compatible with the drug to be administered. Such substances include but are not limited to poly(vinyl alcohol), polymers and copolymers of polyacrylamide, ethylacrylate and vinylpyrrolidone, as well as crosslinked polypeptides or polysaccharides, such as chitin.

Capsule-type delivery systems will also find use with the instant invention. These systems, described in Ueno, N., et al., supra, utilize polymer membranes to control the release of the drug in question. These devices are particularly useful for the delivery of hydrophilic drugs. Hydrophobic drugs can be administered via a silicone rubber device such as described in Ueno, N., et al., supra.

Ophthalmic ointments will include a base, generally composed of white petrolatum and mineral oil, often with anhydrous lanolin. Polyethylene-mineral oil gel is also satisfactory, as are other substances that are nonirritating to the eye, permit diffusion of the drug into the ocular fluid, and retain activity of the medicament for a reasonable period of time under storage conditions. If suspensions are used, the particle sizes therein should be less than 10 um to minimize eye irritation. Furthermore, if solutions or suspensions are used, the amount delivered to the patient should not exceed 75 ul, preferably 50 ul or less, to avoid excessive spillage from the eye.

A wide range of polypeptides will find use in the subject compositions. Exemplary polypeptides and their approximate molecular weights can be seen in Table 1. The invention is particularly useful for the administration of such peptide hormones as insulin, thyrotrophin releasing hormone (TRH), luteinizing hormone releasing hormone (LHRH), oxytocin, vasopressin, lypressin, growth hormone releasing factor, gonadotropin releasing hormone, somatotropin, somatostatin, secretin, calcitonin, among others; peptide analgesics such as but not limited to enkephalins including leu- and met- enkephalin and endorphins such as alpha-neoendorphin, beta-neoendorphin, dynorphin A and dynorphin B; glucagon, concanavalin, ribonuclease, lysozyme and ACTH. Generally, any peptide capable of sustaining biological activity when present in the systemic circulation will find use with the subject invention.

The amount of peptide present in the compositions will vary according to the peptide used, condition, and age and size of the subject being treated. Doses can be readily determined by one of skill in the art. Generally, however, the concentration of peptide administered should not exceed 10% (w/v) of the composition, less the isotonic environment of the eye will be significantly disturbed. Thus, since the delivery of 50 ul or less of the peptide composition is preferred, the amount of peptide present int he composition will generally be 5 mg or less (50 ul of a 10% solution).

A permeation enhancer can be coadministered with the peptide drug, either simultaneously as part of the composition, or shortly before or after delivery of the peptide. The use of a permeation enhancer aids absorption of the drug into systemic circulation via the mucous membrane and allows the delivery of less concentrated substances to the eye. Thus, a wider range of peptide drugs can be administered without disturbing the isotonicity of the tear fluid. Such enhancers are particularly useful with

TABLE 1

Exemplary Polypeptides for use with the Subject Invention

| Polypeptide | Molecular Weight |
|---|---|
| Thyrotrophin Releasing Hormone (TRH) | 360 |
| Leucine-Enkephalin | 600 |
| Methionine-Enkephalin | 600 |
| Somatotropin | 800 |
| Oxytocin | 1,000 |
| Vasopressin | 1,000 |
| Lypressin | 1,000 |
| alpha-Neoendorphin | 1,100 |
| beta-Neoendorphin | 1,100 |
| Luteinizing Hormone Releasing Hormone (LHRH) | 1,200 |
| Dynorphin A | 1,400 |
| Dynorphin B | 1,400 |
| Somatostatin | 1,650 |
| Secretin | 3,000 |
| Calcitonin | 3,400 |
| Glucagon | 3,500 |
| ACTH | 4,500 |
| Growth Hormone Releasing Hormone | 4,800 |
| Insulin | 6,000 |
| Concanavalin | 12,000 |
| Ribonuclease | 13,000 |
| Lysozyme | 15,000 | polypeptides having molecular weights exceeding 5000.

Suitable enhancing agents include either alone or in combination, surfactants such as saponins, polyoxyethylene, polyoxyethylene ethers of fatty acids such as polyoxyethylene 4-, 9-, 10-, and 23-lauryl ether, polyoxyethylene 10- and 20-cetyl ether, polyoxyethylene 10- and 20-stearyl ether, sorbitan monooleate, sorbitan monolaurate, polyoxyethylene monolaurate, polyoxyethylene sorbitans such as polyoxyethylene sorbitan monolaurate, decamethonium, decamethonium bromide, and dodecyltrimethylammonium bromide; chelators such as EDTA and disodium EDTA; bile salts and acids such as cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, and urosdeoxycholic acid; fusidic acid derivatives, glycyrrhizic acid, and ammonium glycyrrhizide, with saponin EDTA, fusidic acid, polyoxyethylene 9-lauryl ether, polyoxyethylene 20-stearylether, and glycocholate being preferred.

The concentration of enhancer administered should be the minimum amount needed to sufficiently increase absorption through the mucous membrances of the nasolacrimal duct so as to avoid use of high concentrations of drug that might cause irritation to the eye. Generally, concentrations ranging from 0.1% to 5% (w/v), more preferably 00.25% to 2%, will find use with the subject compositions.

Peptidase inhibitors may also be coadministered, either as constituents of the subject compositions, or shortly before or after delivery of the peptide drug, to inhibit the activity of peptidases present in the eye. Representative peptidase inhibitors include Leu-Leu, bestain, D,L-thiorphan, puromycin, captopril, bacitracin, phenylmethyl sulfonyl fluoride, leupectin, pepstatin A, and aprotinin. The concentration of inhibitor present will depend on the particular peptidase inhibitor used. Concentrations for representative inhibitors are given below in the examples.

Generally, the compositions of the present invention will be administered as often as needed to sustain the proper blood concentration of the drug being so delivered. Systemic blood concentrations can be monitored and the amount and frequency of administration determined accordingly by one of ordinary skill in the art. The compositions can be formulated to allow for the slow, controlled release of the peptide drug into the eye.

Below are examples of specific embodiments for carrying out the present invention. The examples are offered for illustrative purposes only, and are not intended to limit the scope of the present invention in any way.

EXAMPLES

Example 1

Systemic Delivery of Insulin through the Eyes

A. Materials

Commercially available U-500 regular porcine insulin (Iletin® II, containing 500 U/ml) was obtained from Eli Lilly (Indianapolis, IN). Radioactive $^{125}$I-insulin (porcine) was purchased from DuPont NEN Research Products (Wilmington, DE, with a specific activity of 94.9 uCi/ug). Alloxan monohydrate, saponin, insulin and leucine-leucine were purchased from Sigma Chemical Company (St. Louis, MO). all peptides were dissolved in phosphate buffered saline (PBS) at a pH of 7.4 to a final concentration of 0.125%, 1%, 2% or 5% (w/v) along with the radioactive peptides (0.625 uCi/25 ul). A radioactive solution of 1%, 2% and 5% insulin in 1% saponin was also prepared in PBS.

B. Methods

To induce hyperglycemia in rabbits, a 10% solution of alloxan monohydrate was prepared in citrate-phosphate buffer at a pH of 3.5–4.0. The solution was sterilized by filtering through a Millipore filter and was kept in the refrigerator before use. New Zealand white rabbits weighing 2–3 kg were fasted for 24 hrs before injection with alloxan. The animals were anesthetized with ketamine HCl and zylazine during the injection of 10% alloxan (100 mg/kg) into the marginal ear vein at a rate of 0.5 ml/min. Hyperglycemia, with blood glucose over 300 mg %, developed 3 days after alloxan injection. Blood glucose levels were determined before, and at least twice weekly after alloxan injection, using one drop of fresh whole blood collected by venipuncture and applied to a GLUCOSCAN Test Strip and read one minute later by a GLUCOSCAN ™ 2000 Meter (Lifescan Inc.; Mountain View, CA). Those animals were selected in which the blood glucose levels were greater than 300 mg % for at least two weeks. The control animals (normal) had blood glucose levels of 100 to 150 mg %.

For insulin absorption experiments, normal New Zealand white female rabbits weighing 2.0–3.0 kg were used. The rabbits were anesthetized with 30 mg/kg pentobarbital sodium intravenously through the marginal ear vein. Additional pentobarbital sodium (1 mg/kg/hr) was given throughout the experiment to maintain anesthesia. The femoral artery was cannulated with polyethylene tubing (PE-90) for the collection of blood samples and for the replacement of blood volume with heparinized saline. Twenty-five microliters of insulin solution was instilled into the left eye of the rabbit. 1 ml aliquot of blood was collected from the femoral artery at 0, 5, 10, 20, 30, 60, 90, 120, 150, 180 min and every 1 hr thereafter for a total time period of 12 hrs. The radioactivity of blood samples was counted in a gamma counter (Packard Auto Gamma 500, Packard instrument Company, Downers Grove, IL), and the concentration of insulin absorbed was calculated. At the end of blood collection, the rabbits were euthanized with sodium pentobarbital. The left eye was enucleated and dissected. The cornea, iris, ciliary body, lens, retina and choroid were isolated, and the wet weight of tissues promptly measured. The radioactivity of each tissue sample was determined with a Packard Auto-Gamma Counter and the concentration of insulin in each tissue calculated. The internal standard was prepared by using the diluted insulin (0.0025 uCi/10 ul).

The i.v. injection of insulin at 50 ug (with 0.125 uCi/50 ul of radioactivity) was also carried out. One milliliter of blood sample was collected at 0, 2, 4, 6, 10, 20, 30, 60 90, 120, 150, 180, 240, and 300 minute intervals. The blood volume was replaced by an equal volume of heparinized normal saline. The radioactivity of blood samples was determined with a gamma counter. The concentration of insulin in the blood was expressed in ng/ml. For insulin action in diabetic animals, alloxan-treated rabbits were used. Rabbits were anesthetized with 30 mg/kg pentobarbital sodium intravenously and were then maintained anesthetized with an additional dose of pentobarbital sodium at a rate of 1 mg/kg/hr. Radioactive insulin solution (1% insulin in 1% saponin) was instilled (25 ul for normal rabbits and 50 ul for diabetic animals which were equivalent to approximately 6 U and 12 U insulin, respectively) into the left eyes of 12 hr fasted animals, and 1 ml aliquot of blood samples was collected from the cannulated femoral artery at time intervals specified in the RESULTS section. The blood insulin level was determined in a gamma counter (Packard Auto-Gamma 500, Packard Instrument Company, Downers Grove, IL). The blood glucose was measured on a GLUCOSCAN ™ 2000 Meter.

Figure 7:
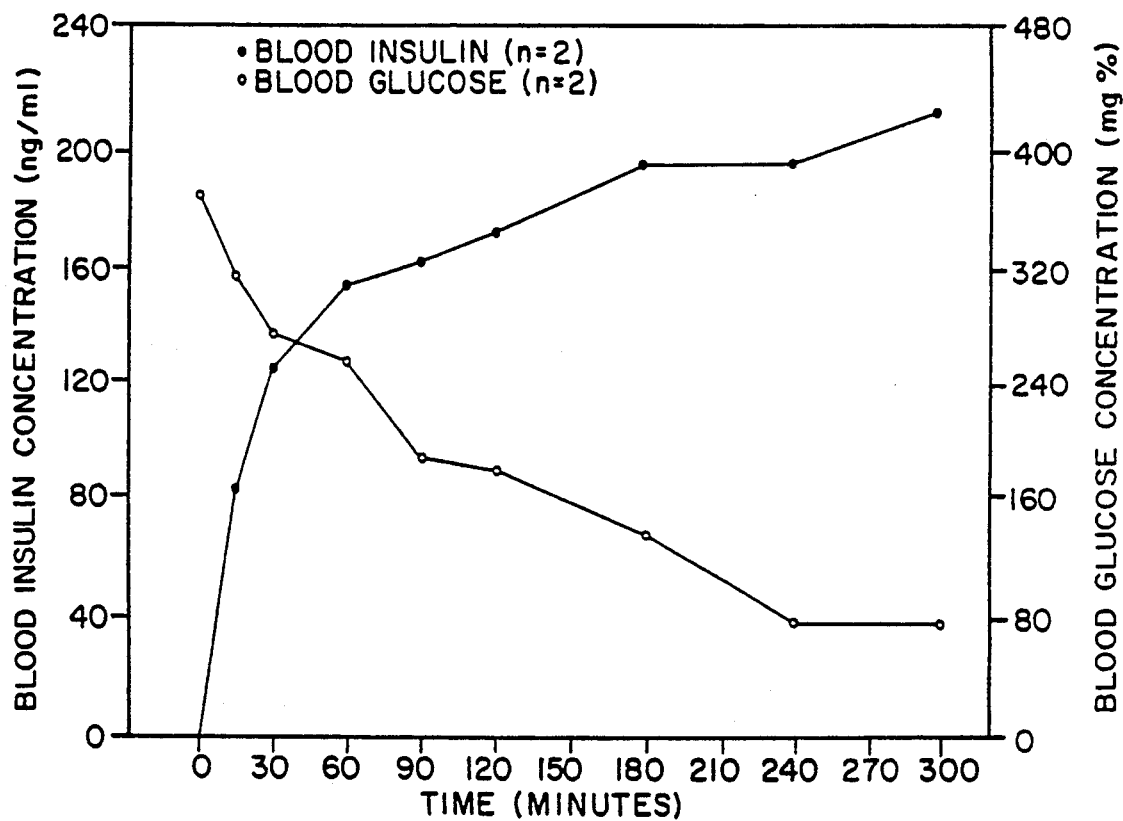
FIG. 7 demonstrates the effect of ocular administration of 1% insulin in 1% saponin on blood glucose concentrations in alloxan-treated diabetic rabbits. Each point is a mean of 2 values.

C. Results 5 and 6). When 50 ul of 1% insulin in 1% saponin was instilled into the eyes of alloxan-treated diabetic animals, the blood glucose of 12 hr fasted animals was reduced from 370 mg % to 185 mg % in 90 min and further to 75 mg % in another 150 min (FIG. 7). Table 2 illustrates the amount of insulin remaining in various eye tissues at the end of a 12 hr experiment. As can be seen, the amount remaining ranged from 0.028-0.049% of the total amount of insulin instilled into the eyes.

TABLE 2

The amount of insulin remaining in eye tissues at the end of 12 hr experiment

Residual amount of insulin remaining in tissues (ng/tissues)

| Tissue | 0.125% insulin (n = 4) | | 1% insulin (n = 5) | | 5% insulin (n = 5) | |
|---|---|---|---|---|---|---|
| | Amount | % of instilled | Amount | % of instilled | Amount | % of instilled |
| Cornea | 5.34 ± 1.56 | 0.0171 ± 0.0050 | 24.68 ± 4.72 | 0.0099 ± 0.0019 | 130.94 ± 24.04 | 0.0105 ± 0.0019 |
| Iris | 0.74 ± 0.27 | 0.0024 ± 0.0009 | 3.59 ± 1.11 | 0.0014 ± 0.0004 | 18.88 ± 3.23 | 0.0015 ± 0.0003 |
| Ciliary-Body | 0.82 ± 0.25 | 0.0026 ± 0.0008 | 3.98 ± 2.94 | 0.0016 ± 0.0012 | 24.13 ± 4.45 | 0.0019 ± 0.0004 |
| Lens | 2.95 ± 0.95 | 0.0094 ± 0.0030 | 11.12 ± 4.84 | 0.0045 ± 0.0019 | 36.80 ± 5.66 | 0.0029 ± 0.0005 |
| Retina | 2.18 ± 0.63 | 0.0070 ± 0.0020 | 8.52 ± 4.54 | 0.0034 ± 0.0018 | 48.75 ± 9.99 | 0.0039 ± 0.0008 |
| Choroid | 3.40 ± 1.11 | 0.0109 ± 0.0036 | 19.09 ± 15.05 | 0.0076 ± 0.0060 | 94.39 ± 26.03 | 0.0076 ± 0.0021 |
| TOTAL | 15.43 ng | 0.0494% | 70.98 ng | 0.0284% | 353.89 ng | 0.0283% |

All data were analyzed with Student's t-test for two values and analysis of variance for more than two values. Each value was expressed as mean±standard error of the mean. A p value of 0.05 or less was considered significant.

Figure 2:
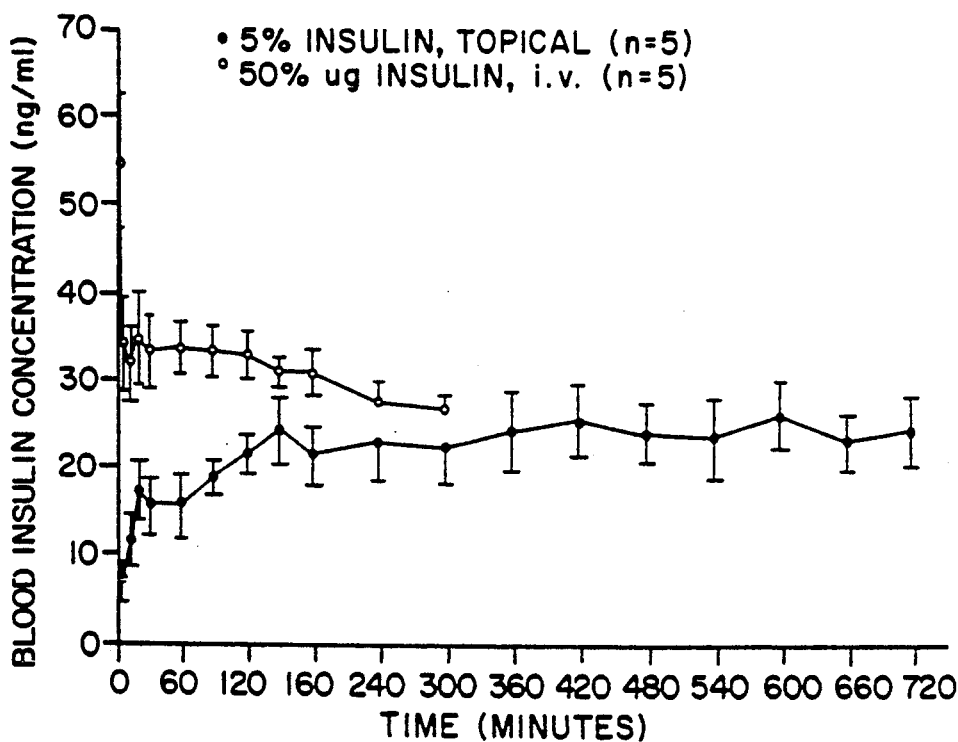
FIG. 2 shows a comparison of blood insulin concentration obtained via i.v. injection to that obtained by topical instillation through the eyes. Each point is a mean of 5 values and the bars represent SEM.

When 0.125% insulin solution was instilled into eyes, it reached 1.3 ng/ml in 11 hrs (FIG. 1). A 1% insulin solution took 8 hrs to reach a plateau concentration of 9 ng/ml (FIG. 1). A 5% insulin solution took only 2.5 hrs to reach a plateau at 24 ng/ml (FIG. 2). These results indicate a good dose-absorption relationship of insulin in the range of 0.125%-5% solutions (FIGS. 1 and 2).

When 50 ug of insulin was injected intravenously, the blood concentration of insulin could be maintained at 27 ng/ml (FIG. 2) which was about the same as that caused by an eye drop of 5% (25 ul) which maintained blood concentration at 25 ng/ml (FIG. 2). These results indicate that ocular administration is comparable with i.v. injection of insulin.

Figure 3:
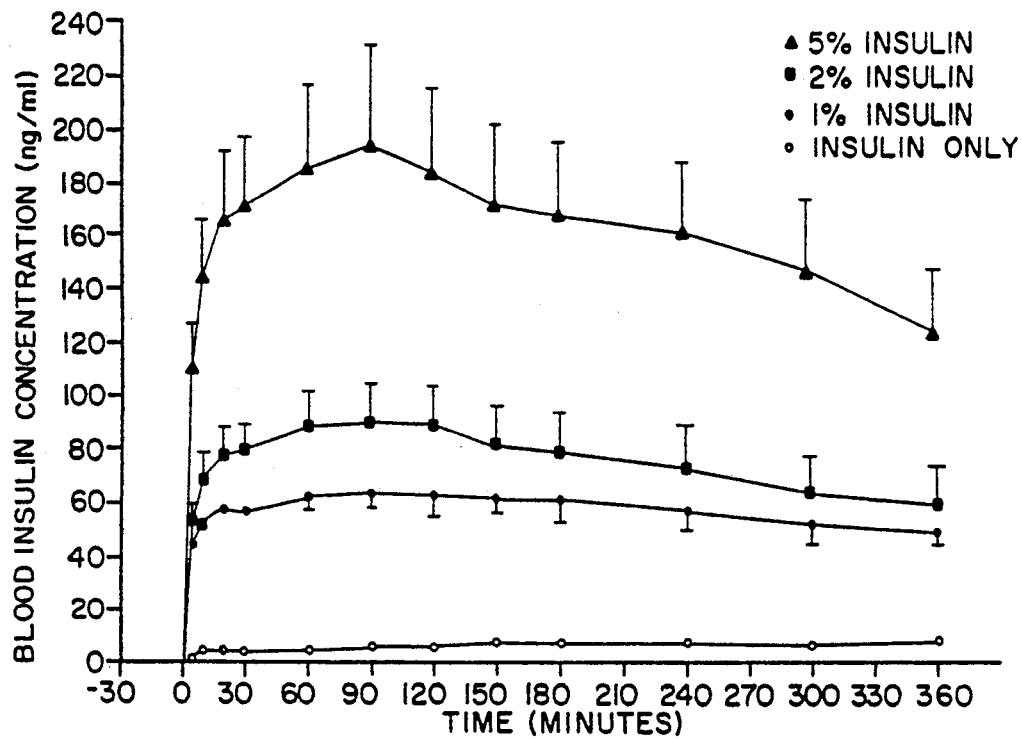
FIG. 3 demonstrates the absorption of various insulin concentrations with the coadministration of 1% saponin into systemic circulation through the eyes. Each point is a mean of 6 values and bars represent SEM.

To test whether the permeation enhancer saponin increased insulin absorption into systemic circulation, 25 ul of 1%, 2% and 5% insulin plus 1% saponin solution were instilled into eyes as above. Blood insulin concentrations reached 63 ng/ml, 89 ng/ml and 195 ng/ml, respectively, in the systemic circulation (FIG. 3). These results indicate that 1% saponin can enhance insulin absorption by at least 7-fold (FIGS. 1, 2 and 3).

A change of pH from 5 to 8 did not affect insulin absorption. Furthermore, the addition of the peptidase inhibitor leucine-leucine did not significantly improve insulin absorption. Without being bound by any particular theory, this result is probably due to the fact that peptidase activity in conjunctiva and tears is low as opposed to peptidase activity in cornal epithelium and iris-ciliary body. Thus, peptides that are not absorbed by the eye but rather remain in the cul-de-sac for absorption into systemic circulation appear relatively safe from degradation.

Figure 4:
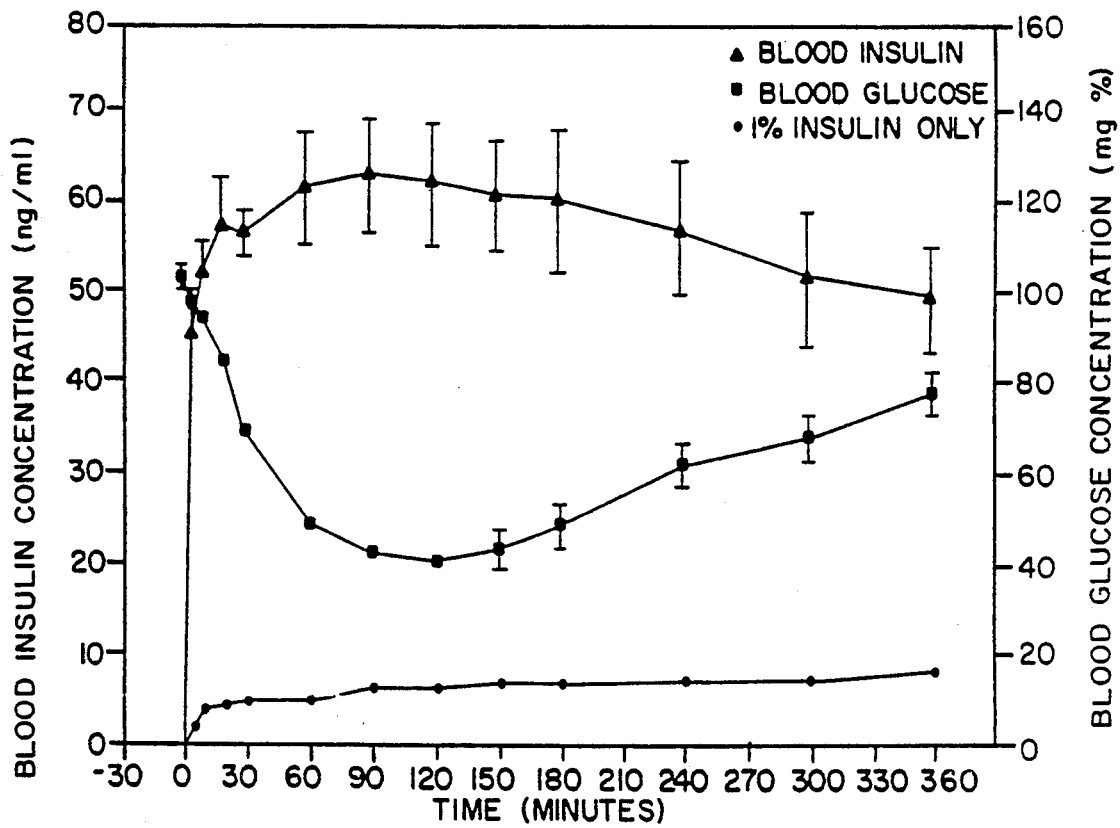
FIG. 4 shows the effect of ocular administration of 1% insulin in 1% saponin on blood glucose concentrations in normal rabbits. Each point is a mean of 6 values and bars represent SEM.
Figure 5:
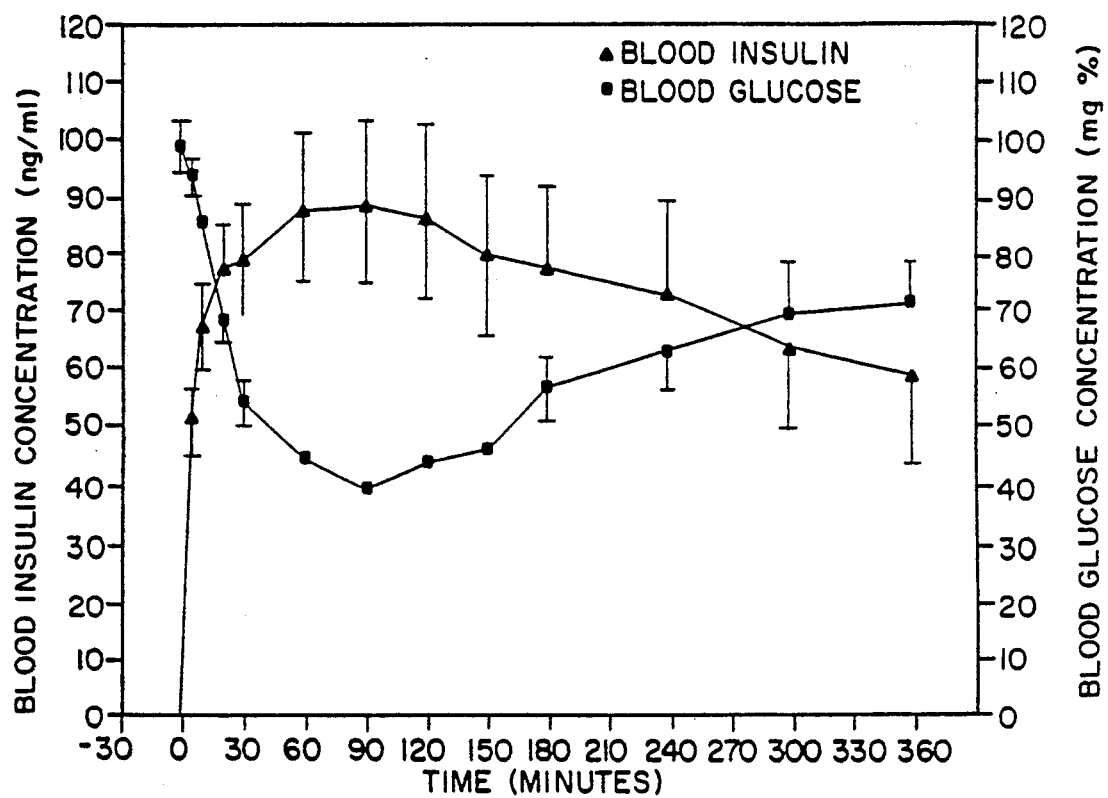
FIG. 5 depicts the effect of ocular administration of 2% insulin in 1% saponin on blood glucose concentration in normal rabbits. Each point is a mean of 6 values and bars represent SEM.
Figure 6:
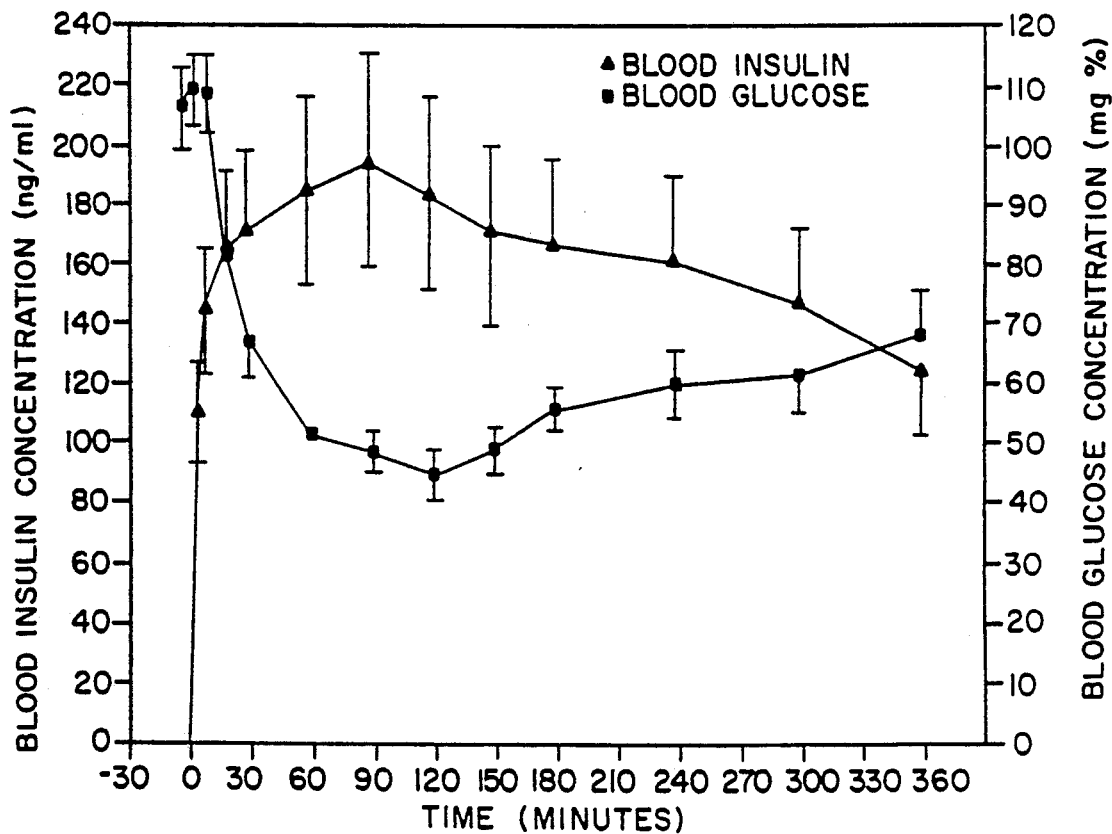
FIG. 6 illustrates the effect of ocular administration of 5% insulin in 1% saponin on blood glucose concentration in normal rabbits. Each point is a mean of 6 values and bars represent SEM.

Most importantly, 25 ul of 1% insulin in 1% saponin was able to lower the blood glucose of 12 hr fasted normal animals from 102 mg % to 50 mg % in an hour. Blood glucose concentrations remained low for at least 3 hrs (FIG. 4). Higher concentrations of insulin (2% and 5%) in 1% saponin were able to depress the blood glucose concentrations to even lower levels (approximately 40-45 mg %) for longer periods of time (FIGS.

This study demonstrates that the ocular nasolacrimal system is a feasible route for insulin absorption into the systemic circulation resulting in a concomitant reduction of blood glucose concentrations in alloxantreated diabetic, as well as normal, animals. Systemic insulin absorption through the eyes can be improved by an absorption enhancer, saponin, to facilitate its absorption. With 1% saponin, the blood concentration of insulin can reach at least 7-fold higher levels than without saponin; the blood glucose concentrations can also reach lower levels for longer periods.

EXAMPLE 2

Increased Systemic Insulin Absorption Using Permeation Enhancers

To test the ability of various permeation enhancers to increase insulin absorption, the following experiment was conducted.

A. Materials

Insulin, sodium glycocholate, decamethonium bromide, polyoxyethylene-9-lauryl ether (BL-9), polyoxyethylene sorbitan monolaurate (tween 20), saponin, EDTA, and sodium fusidate were purchased from Sigma Chemical Company (St. Louis, MO). $^{125}$I-insulin (Spec. Act. 94 uCi/ug) was purchased from DuPont NEN Research Products (Wilmington, DE). All agents were dissolved in phosphate buffered saline (PBS) at pH 7.4 along with radioactive insulin.

B. Methods

New Zealand white female rabbits weighing 2.0-3.0 kg were used. The rabbits were anesthetized with 30 mg/kg were used. The rabbits were anesthetized with 30 mg/kg pentobarbital sodium intravenously through the marginal ear vein. Additional pentobarbital sodium (1 mg/kg/hr) was given throughout the experiment to maintain anesthesia. The femoral artery was cannulated with polyethylene tubing (PE-90) for the collection of blood samples and for replacement of blood volume with heparinized (50 U/ml) normal saline. 25 ul of radioactive insulin solution (0.625 uCi/25 ul) was instilled into the left eye of the rabbit. 1 ml aliquot of blood was collected from the femoral artery at 0, 5, 10, 20, 30, 60, 90, 120, 150 and 180 min and every 1 hr thereafter for a total time period of 6 hrs. The radioactivity of blood samples was counted in a gamma counter (Packard Auto-Gamma 500, Packard Instrument Company, Downers Grove, IL) and the concentration of insulin absorbed was calculated. Blood glucose levels were determined using one drop of fresh whole blood collected by venipuncture and applied to a GLUCOSCAN Test Strip and read one minute later by a GLUCOSCAN ™ 2000 Meter (Lifescan inc., Mountain view, CA). At the end of blood collection, the rabbits were euthanized with an overdose of sodium pentobarbital. The internal standard was prepared by using the diluted corresponding insulin (0.0025 uCi/10 ul). The concentration of insulin equivalent in the blood was expressed in ng/ml.

C. Results

All data were analyzed with Student's t-test for two values and analysis of variance for more than two values. Each value was expressed as mean±standard error of the mean. A p value of 0.05 or less was considered significant.

Figure 10:
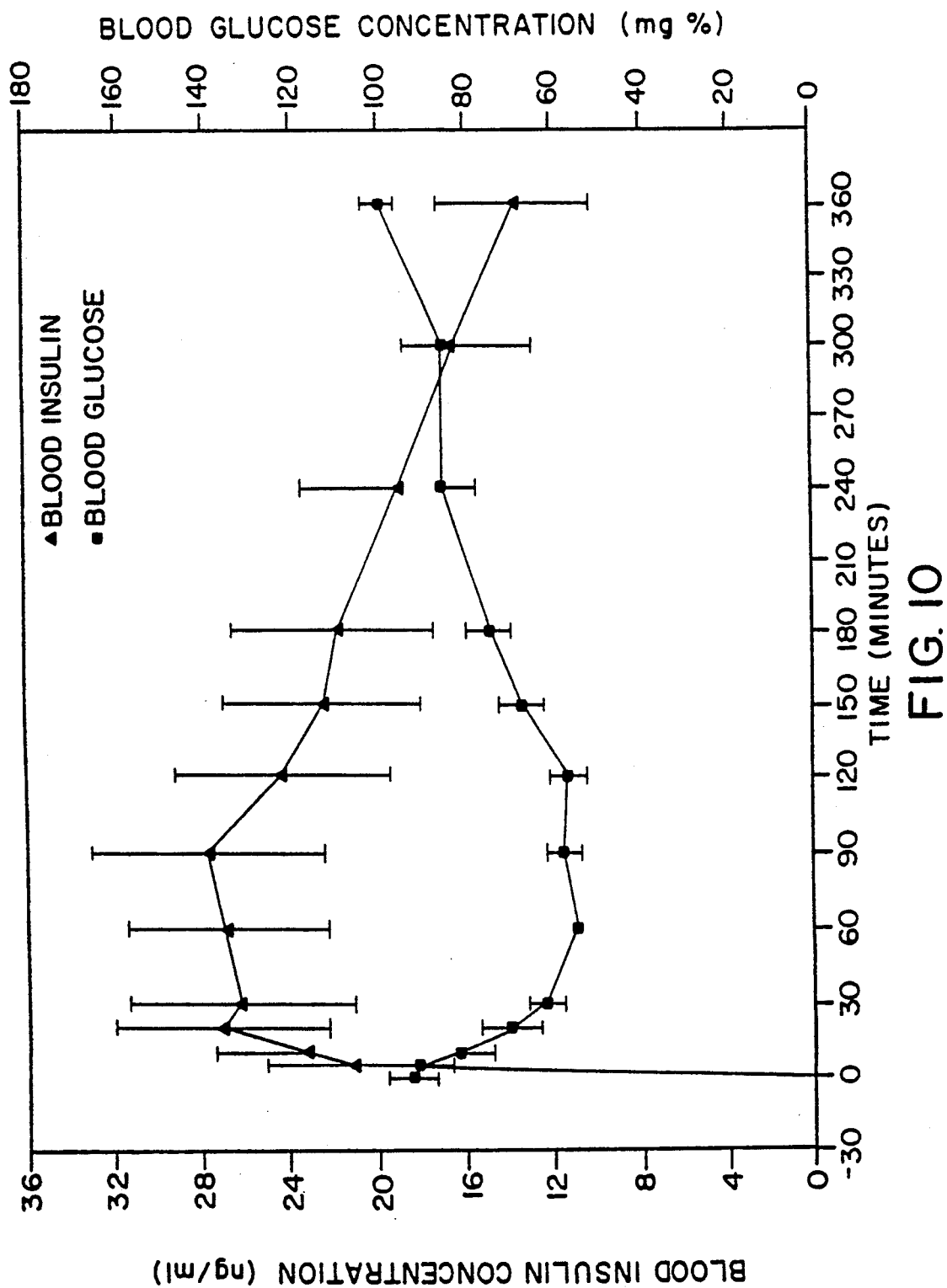
FIG. 10 demonstrates the effect of 0.5% saponin on the uptake of a 1% insulin solution and on blood glucose concentration. Each point is a mean of 6 values and bars represent SEM.

When 1% insulin was instilled to the eye, the blood concentration reached only 6.5 ng/ml (FIG. 10).

Glycocholate is an anionic detergent and a bile salt. 1% enhanced the insulin absorption approximately 2-fold and reduced the blood glucose from 108 mg % to 94 mg % (Table 3).

Decamethonium is a cationic detergent which did not significantly improve the insulin absorption nor reduce the blood glucose (Table 3).

Polyoxyethylene 9-lauryl ether (BL-9) is a nonionic detergent 1% of which enhanced insulin penetration at least 3-fold and markedly reduced the blood glucose from 97 mg % to 56 mg % (Table 3).

Tween 20 (1%) behaved similarly with decamethonium, showing only a slight increase in insulin absorption and a minute reduction in blood glucose concentration (Table 3).

EDTA is a chelating agent which can loosen intercellular tight junction. 1% of EDTA increased insulin penetration 3-fold and reduced blood glucose concentration significantly from 94 mg % to 64 mg % (Table 3).

Figure 12:
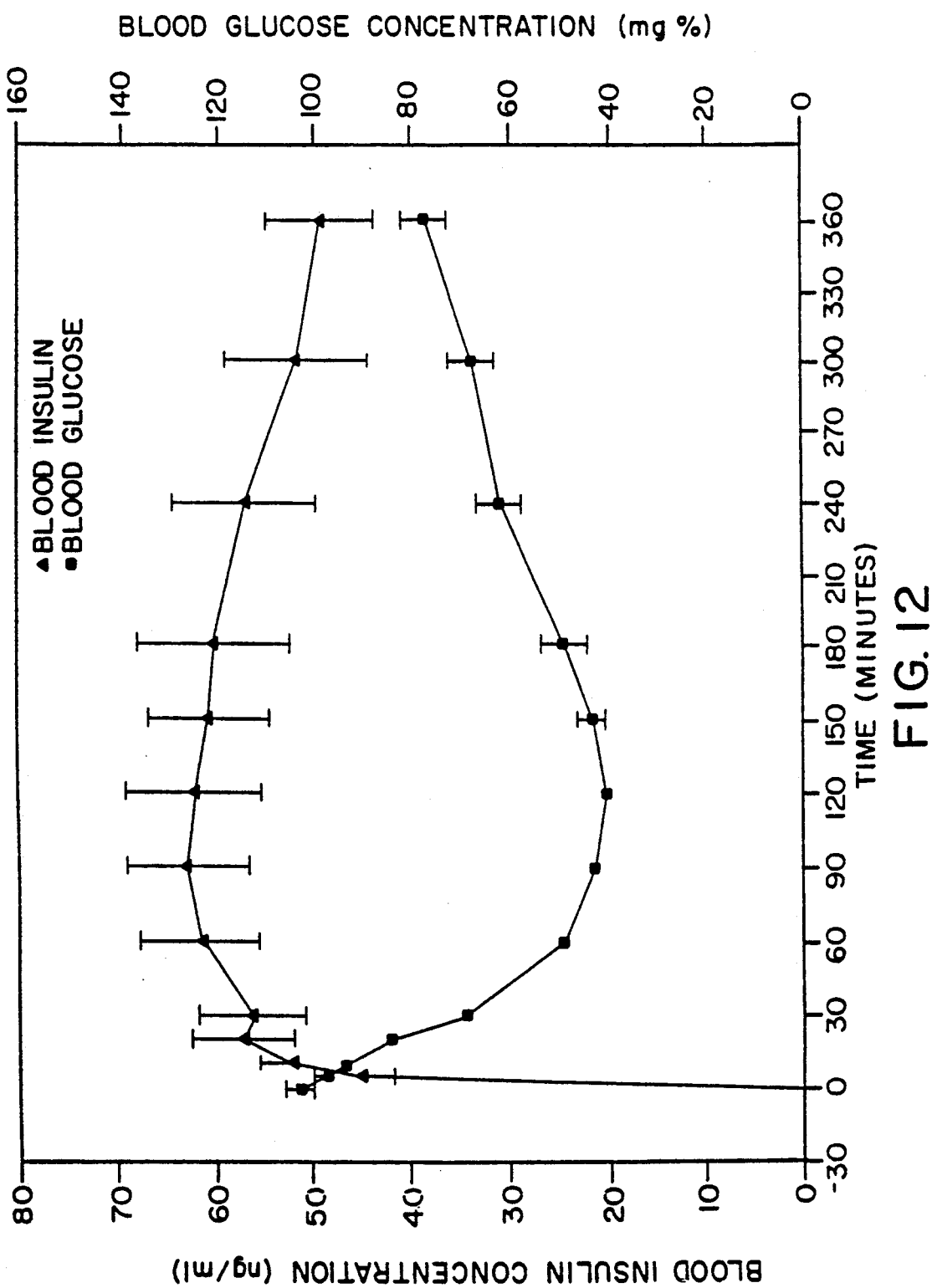
FIG. 12 shows the effect of 1% saponin on the absorption of a 1% insulin solution and blood glucose concentration. Each point is a mean of 6 values and bars represent SEM.

Fusidic acid (1%) showed marked enhancement of insulin absorption (approximately 4-fold) and significant reduction in blood glucose concentration from 90 mg % to 51 mg % (Table 3).

among all agents tested saponin (1%) showed the most potent efficacy to enhance insulin absorption (approximately 10-fold) and reduce blood glucose form 102 mg % to 41 mg % (FIG. 12; Table 3).

TABLE 3

Effects of Absorption Enhancers on Insulin Penetration and Blood Glucose Concentrations

| Absorption Enhancer (1% Solution) | Insulin peak Concentration (ng/ml) | Blood Glucose Concentration (mg %) Before | After | % Change in Blood Glucose Concentration |
|---|---|---|---|---|
| Control | 6.5 ± 0.8 | 93 ± 2 | 94 ± 3 | no change |
| Saponin | 63.0 ± 6.3 | 102 ± 4 | 41 ± 2 | 60 |
| Fusidic acid | 26.5 ± 4.5 | 90 ± 3 | 51 ± 2 | 43 |
| BL-9 | 20.0 ± 1.8 | 97 ± 2 | 56 ± 3 | 42 |
| EDTA | 22.5 ± 5.7 | 94 ± 3 | 64 ± 5 | 32 |
| Glycocholate | 13.3 ± 1.4 | 108 ± 7 | 94 ± 4 | 13 |
| Decamethonium | 10.8 ± 1.8 | 90 ± 3 | 83 ± 2 | 8 |

TABLE 3-continued

Effects of Absorption Enhancers on Insulin Penetration and Blood Glucose Concentrations

| Absorption Enhancer (1% Solution) | Insulin peak Concentration (ng/ml) | Blood Glucose Concentration (mg %) Before | After | % Change in Blood Glucose Concentration |
|---|---|---|---|---|
| Tween 20 | 8.8 ± 0.9 | 90 ± 3 | 77 ± 9 | 14 |

The eye drops contained 1% insulin plus 1% absorption enhancer.

Various concentrations of saponin were tested to study the dose-potency effect of saponin on blood glucose levels and enhanced insulin absorption. It was found that an increase of saponin concentration beyond 1% did not significantly increase insulin absorption nor reduce blood glucose concentration (FIG. 8).

Figure 8:
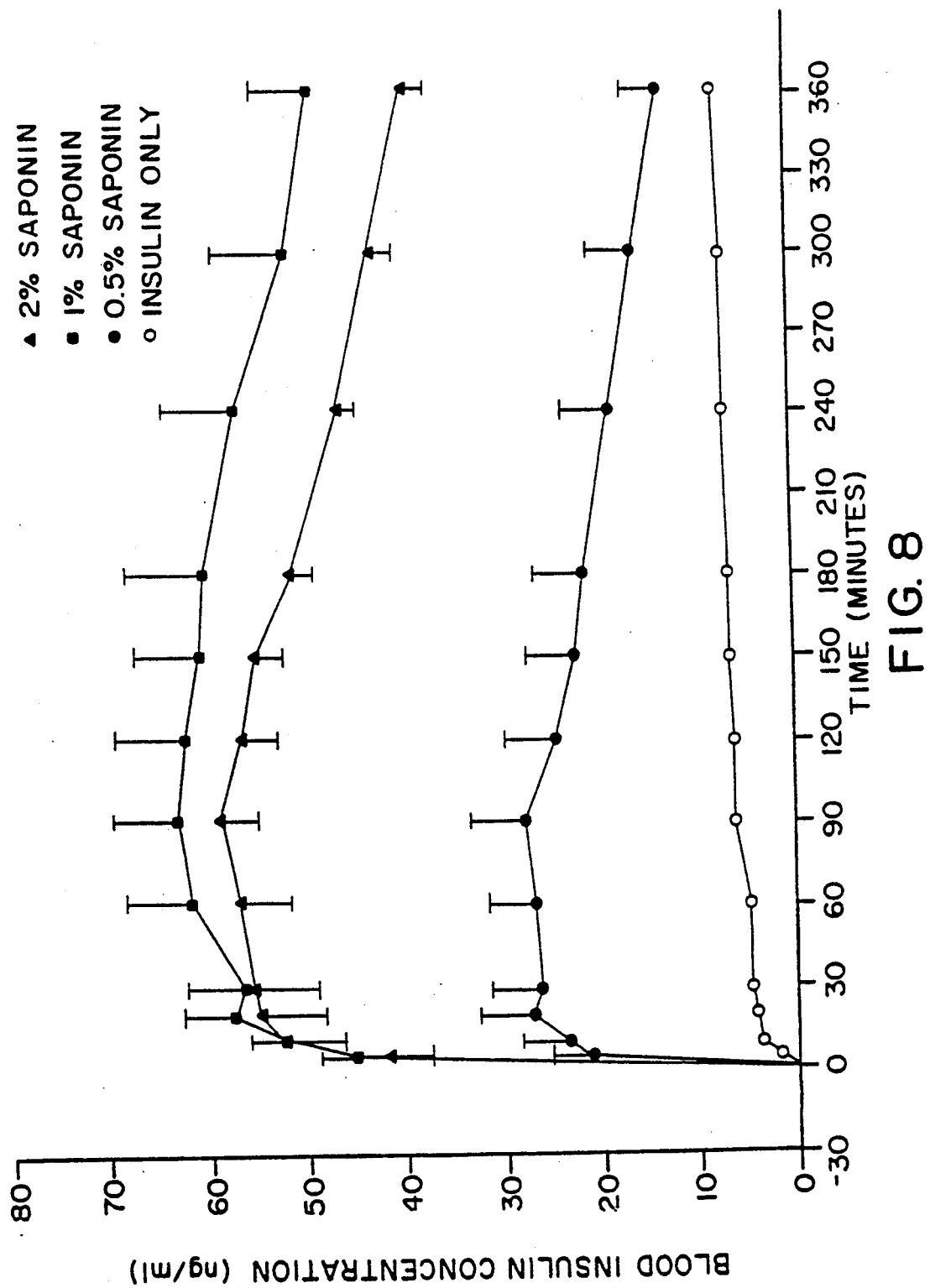
FIG. 8 shows the effect of various concentrations of saponin on absorption of a 1% insulin solution. Each point is a mean of 6 values and bars represent SEM.
Figure 9:
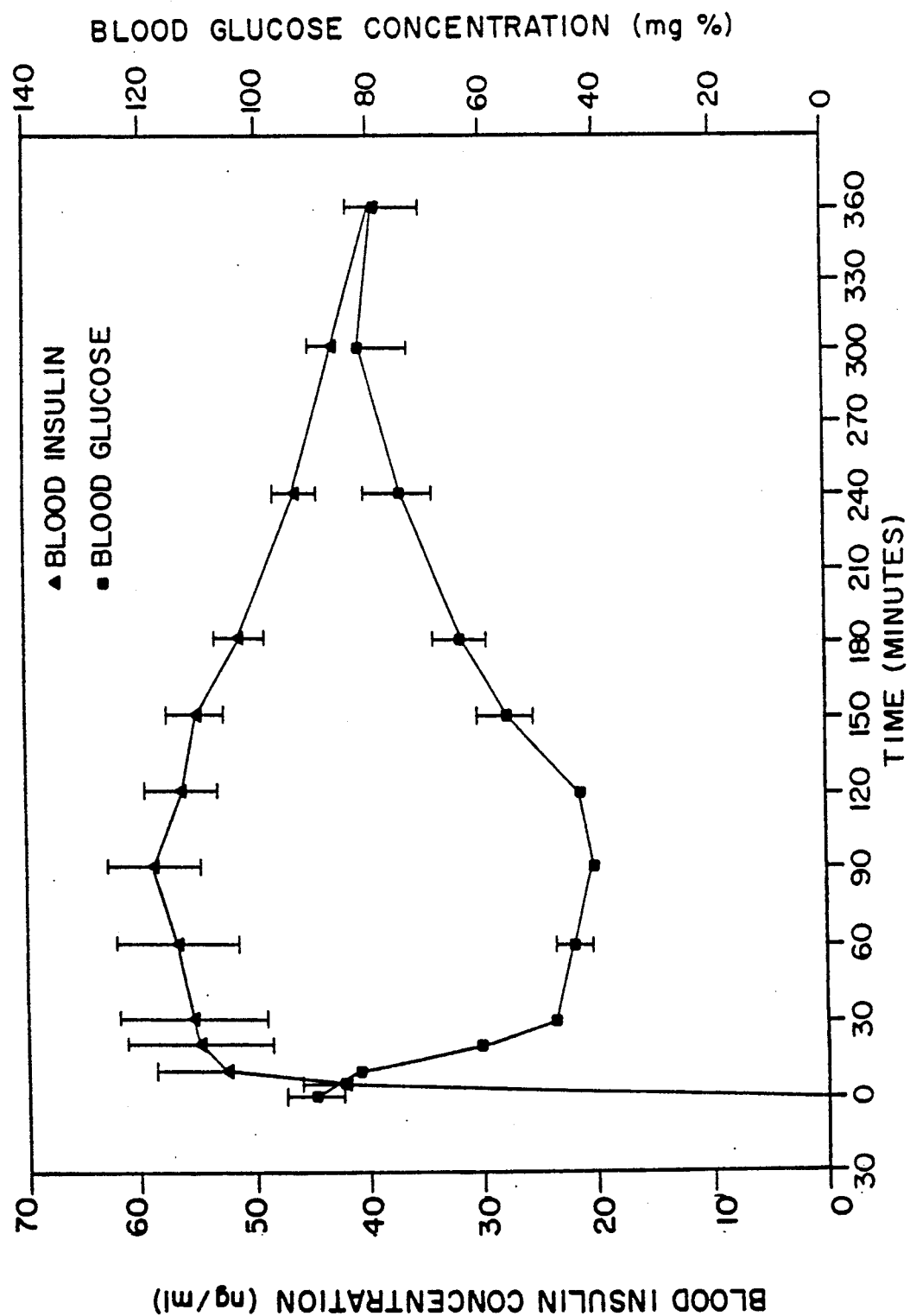
FIG. 9 depicts the effect of 2% saponin on the uptake of a 1% insulin solution and on blood glucose concentration. Each point is a mean of 6 values and bars represent SEM.
Figure 11:
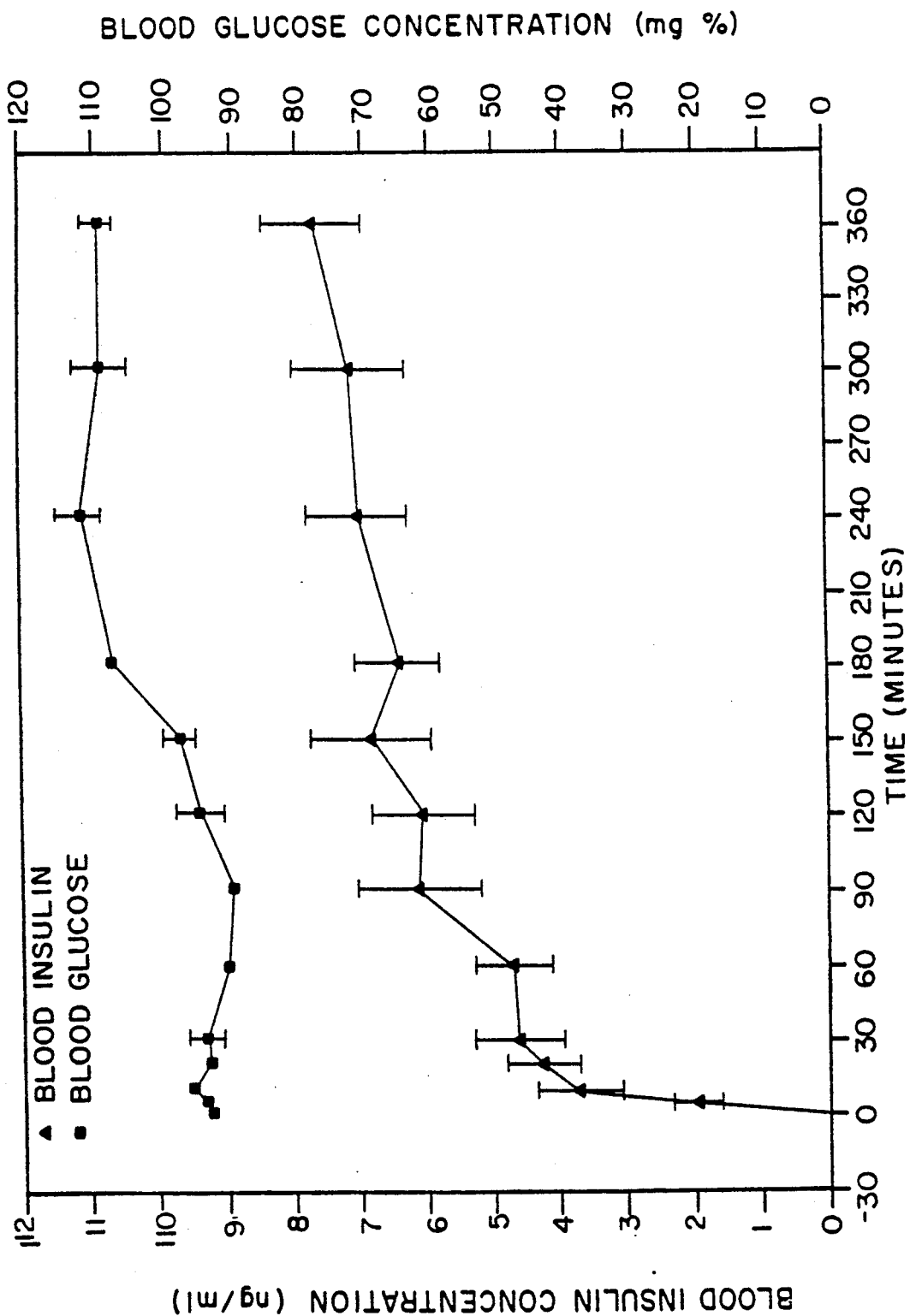
FIG. 11 illustrates the effect of 1% insulin on blood glucose concentration. Each point is a mean of 6 values and bars represent SEM.

However, reduction of saponin concentration from 1% to 0.5% did reduce the ability to enhance insulin absorption and to decrease blood glucose concentration (FIG. 8). The blood glucose concentrations were lowered to about the same extent with 1% insulin plus either 1% or 2% saponin, from 95 mg% to 40 mg% (FIGS. 9 and 12). When 1% insulin alone was instilled, the insulin concentration in the blood (6.5 ng/ml) did not reach the effective concentration (at least 20 ng/ml) to lower the blood glucose concentration (FIG. 11). Without absorption enhancers, an insulin concentration of at least 5% would be required to lower the blood glucose concentration.

Absorption enhancers not only increase insulin uptake into systemic circulation but also into eyeballs as can be seen from Table 3. There was a good correlation between uptake of insulin into systemic circulation and the eyeball (Tables 3 and 4).

Thus, permeation absorption enhancers are useful in increasing systemic absorption. Although the above studies were performed using insulin only, these enhancers also find utility with other peptide drugs (described below), particularly larger peptides.

TABLE 4

Effects of Absorption Enhancers on the Penetration of Insulin into Eyeballs

| 1% insulin plus enhancer | % of insulin taken up by the eyeball | Absolute amount of insulin in the eyeball |
|---|---|---|
| 1% Saponin | 1.9186 | 4796 ng |
| 0.5% Saponin | 0.6733 | 1683 ng |
| 1% Fusidic A | 0.4767 | 1191 ng |
| 1% BL-9 | 0.5221 | 1305 ng |
| 1% EDTA | 0.1684 | 420 ng |
| 1% Glycocholate | 0.0804 | 200 ng |
| 1% C10 | 0.0683 | 170 ng |
| 1% Tween 20 | 0.0771 | 192 ng |
| Control (1% insulin only) | 0.0744 | 185 ng |

EXAMPLE 3

Systemic Delivery of Glucagon Through the Eyes

Glucagon is useful in the treatment of insulin-induced hypoglycemia. To test whether glucagon could be effectively administered through the eyes, the following experiment was conducted as described in Chiou, C. Y. and Chuang, C. Y. J. Ocular Pharm. (1988) 4:179–186.

A. Materials

Glucagon was purchased from Sigma Chemical Company (St. Louis, MO). Radioactive $^{125}$I-glucagon was obtained from DuPont NEN Research Products (Wilmington, DE, with a specific activity of 131 mCi/mg).

Glucagon was dissolved in phosphate buffered saline (PBS) at pH 7.4 to a final concentration of 0.2% 1% or 5% (w/v) along with the radioactive glucagon (0.625 uCi/25 ul).

B. Methods

New Zealand white female rabbits weighing 2.0–3.0 kg were treated as in Example 2B above, with the exception that 25 ul of radioactive glucagon solution (0.625 uCi/25 ul) was used. At the end of blood collection, the rabbits were euthanized with an overdose of sodium pentobarbital. The left eye was enucleated and dissected. The cornea, iris, ciliary body, lens, retina and choroid were isolated, and the wet weight of tissues promptly weighed. The radioactivity of each tissue sample was also determined with a Packard Auto-Gamma Counter and the concentration of glucagon in each tissue calculated. The internal standard was prepared by using the diluted corresponding glucagon (0.0025 uCi/10 ul). An i.v. injection of glucagon at 50 ug (with 0.125 uCi/50 ul of radioactivity) was also carried out. One milliliter of blood sample was collected at 0, 15, 30, 60, 90, 120, 150, 180, 240, 300, and 360 minutes intervals. The blood volume was replaced by an equal volume of heparinized normal saline. The radio-activity of the blood sample was determined with a gamma counter. The blood glucose was measured on a GLU-COSCAN ™ 2000 Meter. The concentration of glucagon in the blood was expressed in ng/ml.

C. Results

All data were analyzed with the Student's t-test for two values and variance analyzed for more than two values. Each value was expressed as mean±standard error of the mean. A p value of 0.05 or less was considered significant.

Figure 13:
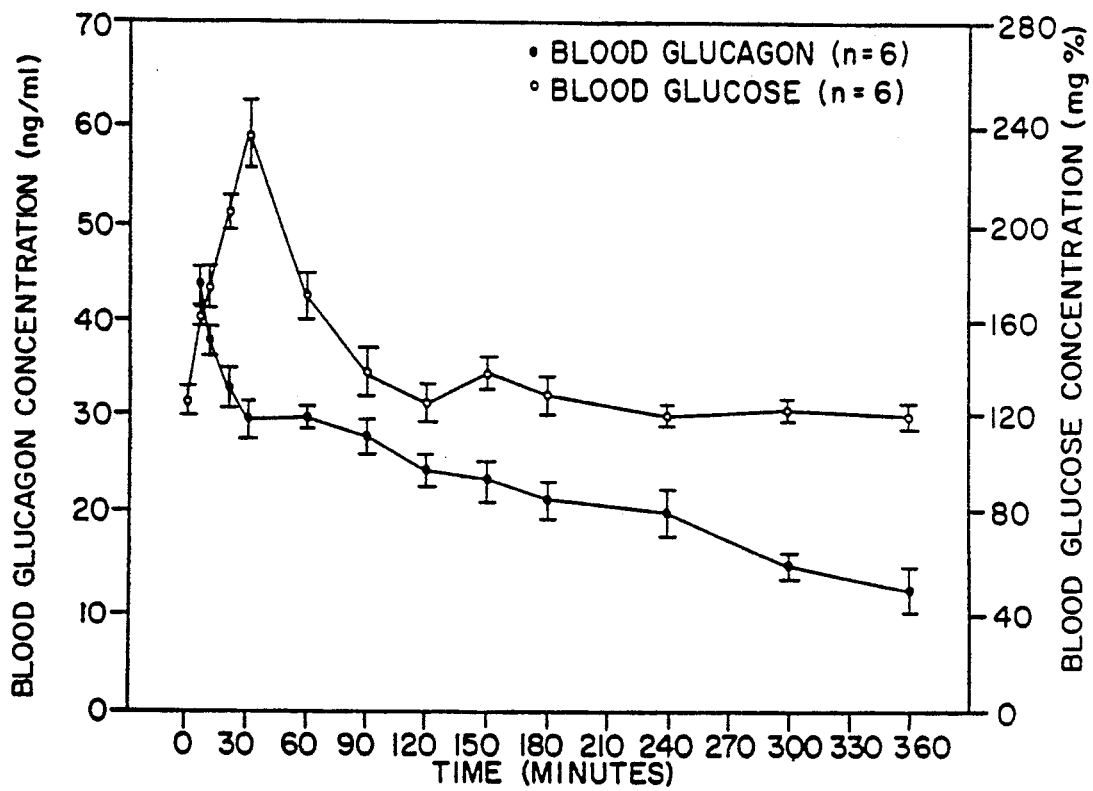
FIG. 13 depicts the effect of an i.v. injection of 50 ug glucagon on blood glucose concentrations in normal rabbits. Bars represent SEM.

The therapeutic dose of glucagon is 1 mg/70 kg or 14.29 ug/kg. Therefore, 50 ug of glucagon was injected i.v. into rabbits of approximately 3 kg (FIG. 13). The blood concentration of glucagon declined rapidly in 30 min and then decreased to 12.5 ng/ml in 6 hrs. The blood glucose concentration increased rapidly after the i.v. injection of glucagon, to reach 235 mg % from 125 mg % as expected. The blood glucose peaked at 30 min after i.v. injection and then reached bottom at 120 min after the injection (FIG. 13).

Figure 14:
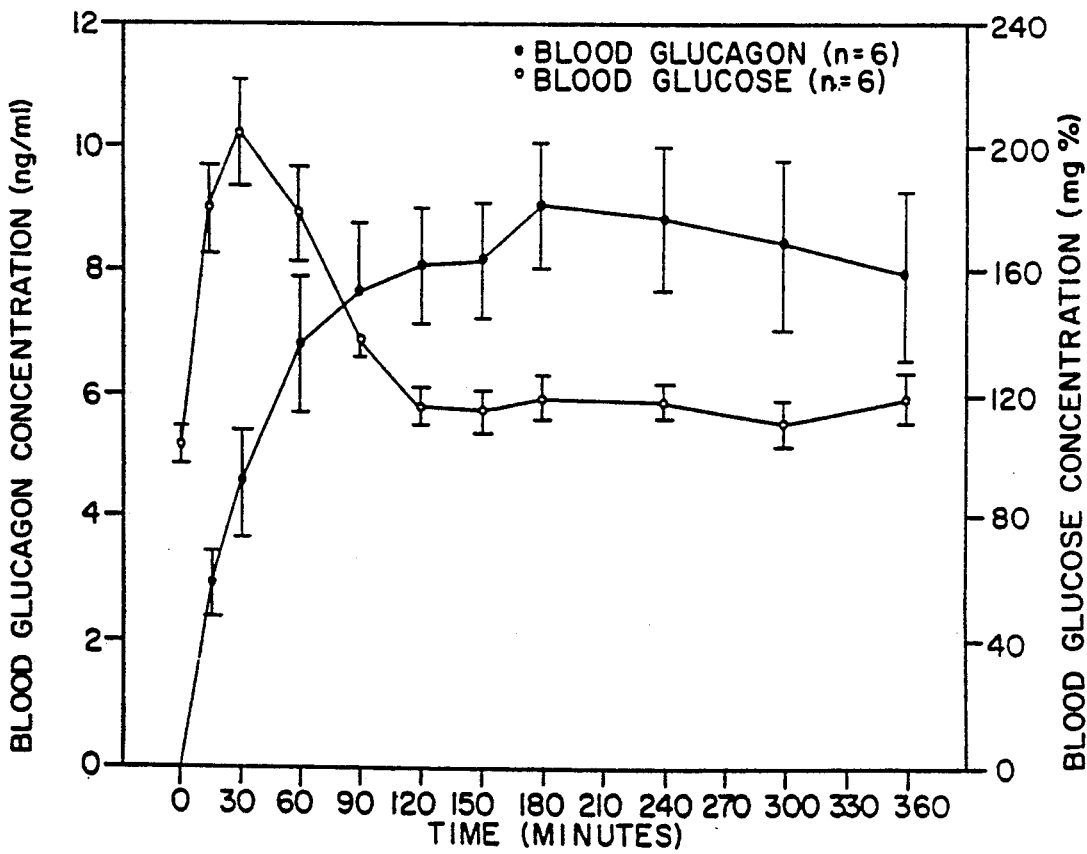
FIG. 14 demonstrates the effect of ocular administration of glucagon (0.2%) on blood glucose concentrations in normal rabbits. Bars represent SEM.
Figure 21:
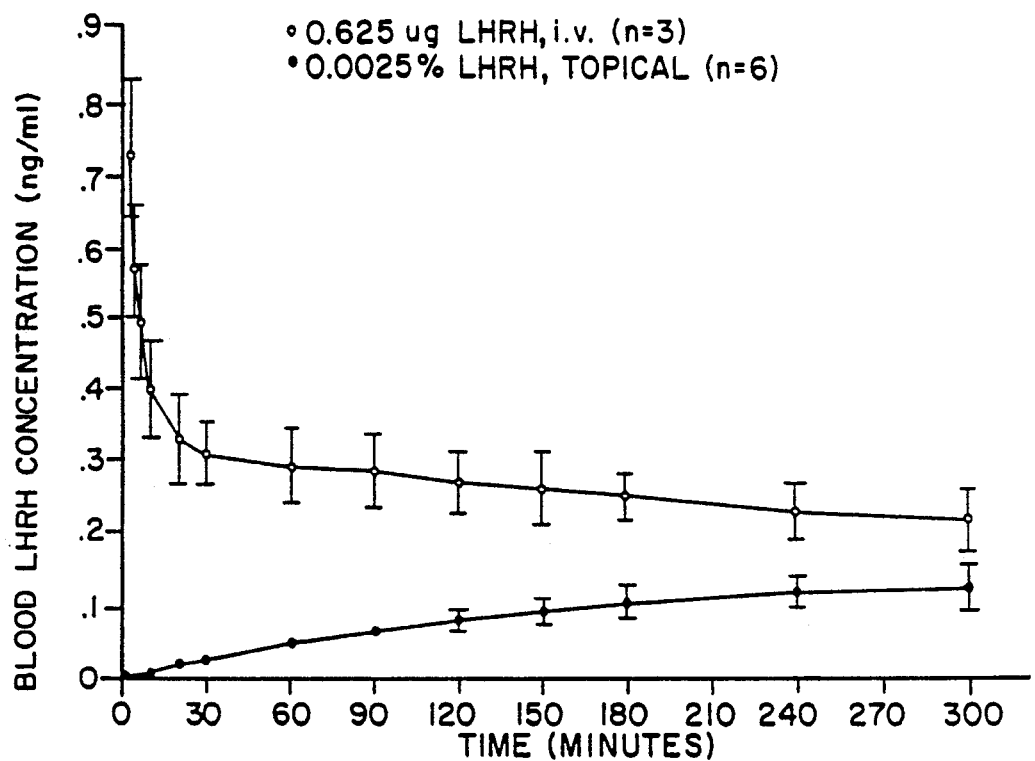
FIG. 21 compares blood LHRH concentration obtained via i.v. injection to that obtained by topical instillation through the eyes. Bars represent SEM.

When 25 ul of 0.2% glucagon (equivalent to 50 ug) was instilled into the left eye, it raised blood glucose effectively to 204 mg % from 104 mg % in 30 min (FIG. 21). The blood glucose concentration came down to 116 mg % in 2 hrs and remained at the same level for the rest of the experiments (6 hrs). The blood glucagon concentration increased gradually and reached the plateau at 8 ng/ml in 2 hrs and remained there for the rest of the experiments (FIG. 14).

Figure 15:
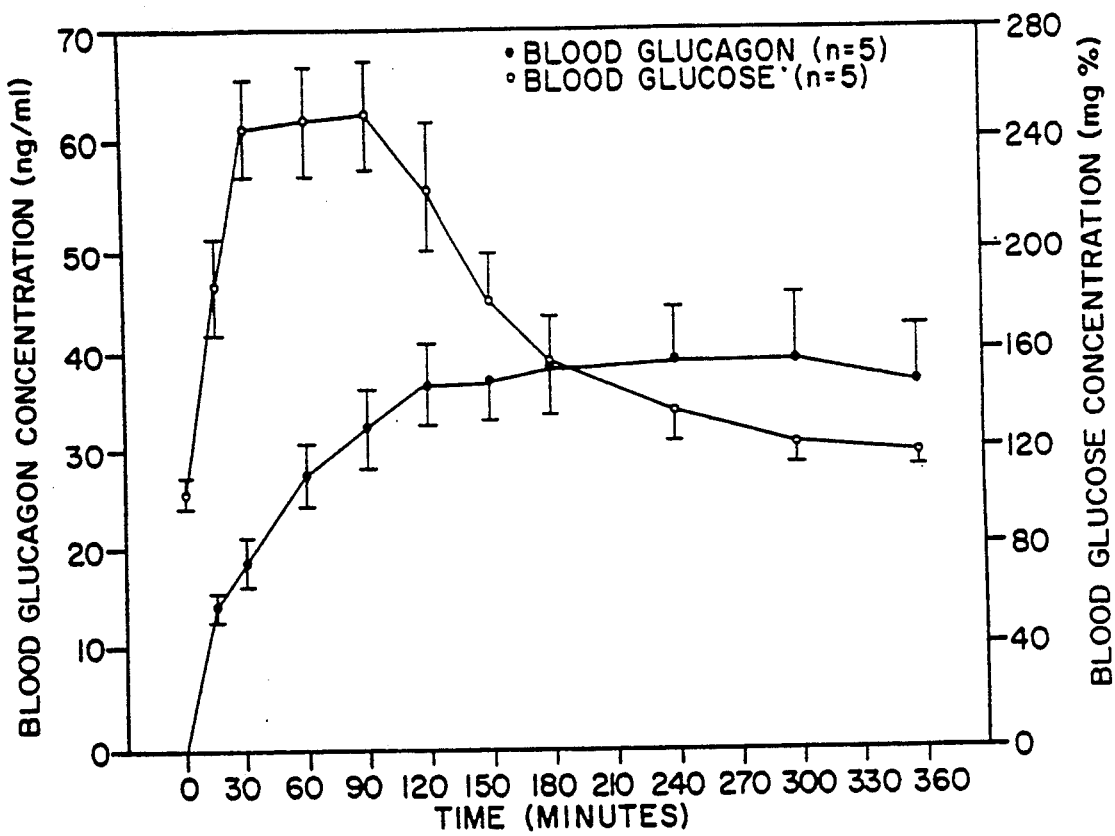
FIG. 15 illustrates the effect of ocular administration of glucagon (1%) on blood glucose concentrations in normal rabbits. Bars represent SEM.

When 25 ul of 1% glucagon (equivalent to 250 ug) was instilled into the left eye, it raised blood glucose concentration to 248 mg % from 103 mg % in 30 min and then remained high for another 60 min (FIG. 15). The blood glucose concentration of glucagon reached the plateau at 37 ng/ml in 2 hrs and then remained high during the rest of the experiments (FIG. 15).

Figure 16:
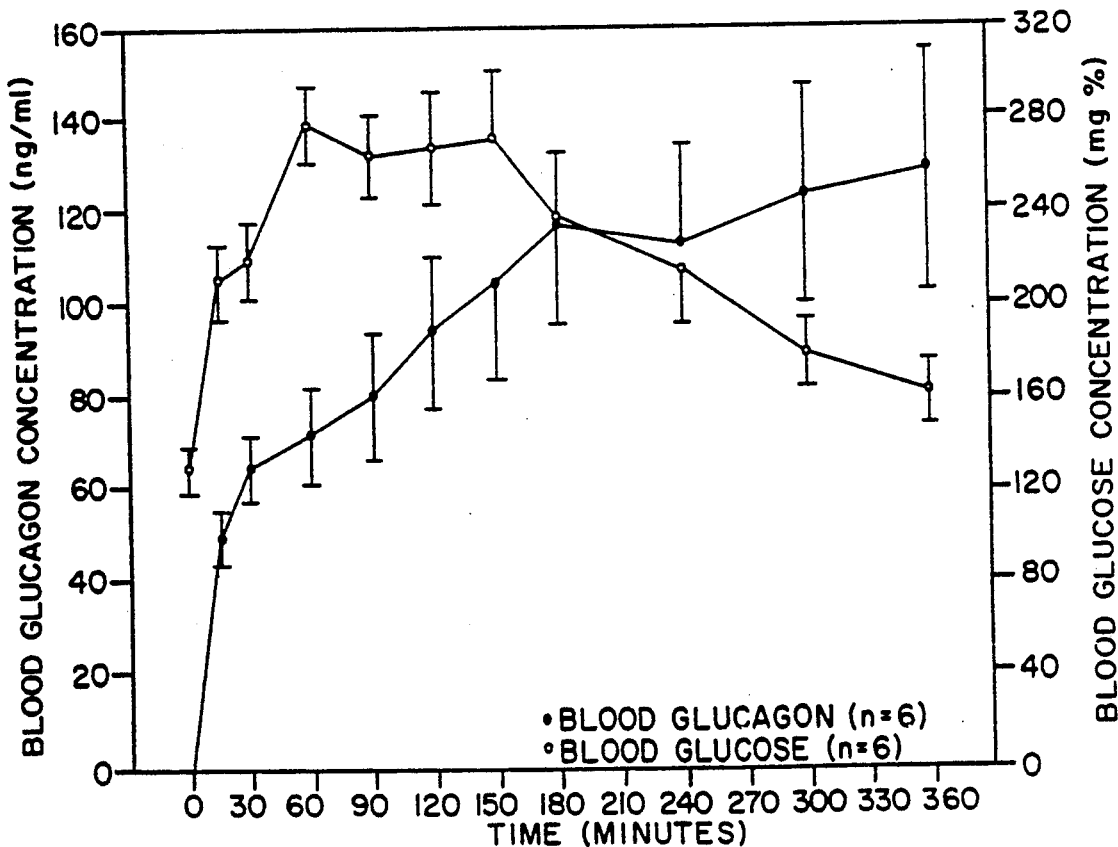
FIG. 16 shows the effect of ocular administration of glucagon (5%) on blood glucose concentrations in normal rabbits. Bars represent SEM.

When 25 ul of 5% glucagon (equivalent to 1250 ug) was instilled, the blood concentration of glucagon kept rising during the experimental period of 6 hrs to reach 130 ng/ml (FIG. 16). The blood glucose concentration rose quickly to 276 mg % from 130 mg % in 60 min and remained high for the next 90 min. The blood glucose concentration declined gradually thereafter to reach 160 mg % at the end of the 6 hr experiment period (FIG. 16).

The amount of glucagon taken up into the eyes was minimal at the end of the 6 hr experimental period. Most of the glucagon detected remained in the cornea where the eye drops contacted directly (Table 5). The total amount of glucagon remaining in the eye tissues except cornea was only 0.105%, 0.103% and 0.123% of the absolute quantity of 0.2%, 1% and 5% solutions instilled into the eyes, respectively. Among cornea, iris-ciliary body, lens, retina and choroid, the great majority 71%, 84% and 87%, respectively, remained in the cornea.

TABLE 5

The amount of glucagon remaining in eye tissues at the end of 6 hr experiment

Residual amount of glucagon remaining in tissues (ng/tissues)

| Tissue | 0.2% (n = 7) | | 1% (n = 5) | | 5% (n = 5) | |
| --- | --- | --- | --- | --- | --- | --- |
| | Amount | % of instilled | Amount | % of instilled | Amount | % of instilled |
| Cornea | 128.26 ± 42.99 | 0.2565 ± 0.0860 | 1314.97 ± 364.89 | 0.5260 ± 0.1460 | 9911.85 ± 2625.87 | 0.7930 ± 0.2101 |
| Iris | 10.12 ± 3.99 | 0.0202 ± 0.0080 | 77.22 ± 25.77 | 0.0309 ± 0.0103 | 402.44 ± 90.51 | 0.0322 ± 0.0073 |
| Ciliary-Body | 3.68 ± 1.23 | 0.0074 ± 0.0025 | 25.51 ± 7.63 | 0.0102 ± 0.0031 | 153.14 ± 38.42 | 0.0123 ± 0.0031 |
| Lens | 35.05 ± 15.09 | 0.0701 ± 0.0302 | 135.54 ± 35.75 | 0.0542 ± 0.0143 | 871.05 ± 210.82 | 0.0697 ± 0.0169 |
| Retina | 1.42 ± 0.34 | 0.0028 ± 0.0007 | 6.15 ± 1.90 | 0.0025 ± 0.0008 | 56.28 ± 23.15 | 0.0045 ± 0.0019 |
| Choroid | 2.11 ± 0.54 | 0.0042 ± 0.0011 | 13.07 ± 4.60 | 0.0052 ± 0.0018 | 57.79 ± 13.07 | 0.0046 ± 0.0011 |
| Total | 180.64 ng | 0.3612% | 1572.46 ng | 0.6290% | 11452.55 ng | 0.9163% |

EXAMPLE 4

Systemic Delivery of Enkephalin Peptide Through Eyes

Leu-enkephalin is a peptide demonstrating analgesic action and is readily available commercially. To test whether enkephalin peptide could be effectively administered via the eyes, the method described in Chiou, G.C.Y. et al., Life Sciences (1988) 43:509–514 was followed.

A. Materials

Leucine-enkephalin (5-L-leucine), [$^{125}$I]-(specific activity of 2200 Ci/mmole) was obtained commercially from DuPont NEN Research Products (Wilmington, DE). Enkephalin was dissolved in phosphate-buffered saline (PBS) at pH 7.4 to a final concentration of 0.125%, 1% and 5% (w/v) along with a radioactivity of 0.625 uCi/25 ul.

B. Methods

New Zealand white female rabbits weighing 2.0–3.0 kg were treated as in Example 2B except that 25 ul of radioactive enkephalin solution (0.625 uCi/26 ul) was used and blood samples collected for a total of 12 hours, rather than 6 hours. At the end of blood collection, the rabbits were euthanized as described above, the left eye enucleated and dissected, and tissues analyzed as described in Example 3B. The internal standard was prepared by using the corresponding enkephalin with lower radioactivity (0.0025 uCi/10 ul). The i.v. injection of enkephalin at 50 ug (with 0.125 uCi/50 ul of radioactivity) was also carried out. One milliliter of blood sample was collected at 0, 2, 4, 6, 10, 20, 30, 60, 90, 120, 150, 180, 240, and 300 minutes intervals. The blood sample was replaced by equal volume of heparinized normal saline. The radioactivity of blood samples was determined with a gamma counter. The internal standard was prepared with corresponding radioactive enkephalin solution with a radioactivity of 0.0125 uCi/10 ul. The concentrations of enkaphalin-equivalent in the blood were expressed in ng/ml.

C. Results

All data were analyzed with Student's t-test for two values and analysis of variance for more than two values. Each value was expressed as mean±standard error of the mean. A p value of 0.05 or less was considered significant.

Figure 17:
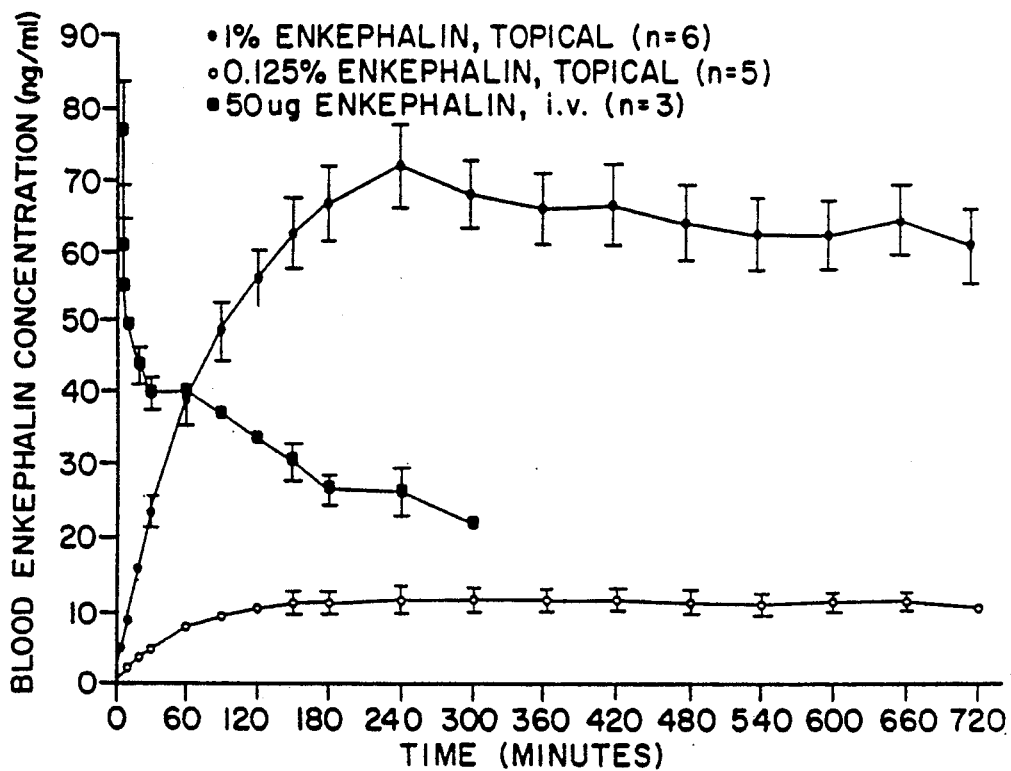
FIG. 17 is a comparison of blood enkephalin-equivalent concentration obtained via i.v. injection to that obtained by topical instillation through eyes. Bars represent SEM.
Figure 18:
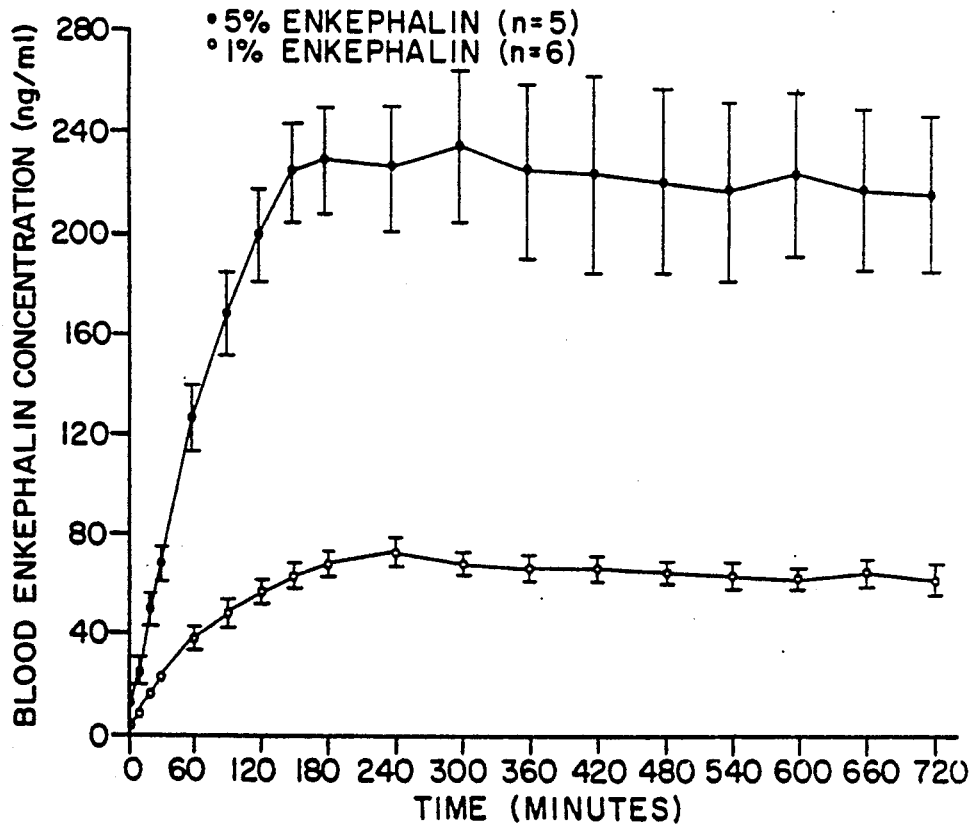
FIG. 18 shows the absorption of enkephalin equivalent into systemic circulation after administration via the eyes. Bars represent SEM.

When 25 ul of 0.125% enkephalin was instilled locally into the left eye, it entered systemic circulation rapidly to reach a plateau of 11.5 ng/ml in 3-4 hrs and remained in the plateau for the rest of experimental period (8-9 hrs) (FIG. 17). With higher concentrations at 1% and 5%, similar absorption kinetics of enkephalin were observed except that they reached higher plateaus of 72 ng/ml and 233 ng/ml, respectively (FIGS. 17 and 18).

Intravenous administration of enkephalin (50 ug i.v.) resulted in rapid decline of blood concentration with a $T_x$ of less than 30 min and reached the lowest point at 22 ng/ml in 5 hrs (FIG. 17). These results indicate that local administration of enkephalin through eyes can maintain a high blood concentration for a long period of time while the blood concentrations of enkephalin decline steadily with i.v. injection.

The residual amount of enkephalin remaining in the eye tissues was minimal at best at 0.12-0.30% of total amount instilled into eyes (Table 6). Most of the enkephalin remained in the cornea where the drug had direct contact with the tissue. Although the total amount of enkephalin in the lens appeared high, it was because of the larger mass of the lens. The actual concentration of enkephalin in the lens was the lowest among all tissues.

EXAMPLE 5

Systemic Delivery Through the Eyes of Polypeptides With Molecular Weights Between 300 and 3500

To test the effectiveness of the subject invention with respect to peptides of varying sizes, the following experiment was conducted as described by Chiou, G. C. Y. and Chuang, C. Y. J., Ocular Pharm. (1988) 4:165-177.

A. Materials

Thyrotrophin-releasing hormone (TRH), luteinizing hormone-releasing hormone (LH/RH) and glucagon were purchased from Sigma Chemical Company (St. Louis, MO). Thyrotropin-releasing hormone, [$^{125}$I]-(spec. act., 2200 Ci/mmole); luteinizing hormone-releasing hormone, $^{125}$I]-(spec. act., 2200 Ci/mmole); and glucagon [$^{125}$I]-(spec. act., 115 mCi/mg) were purchased from DuPont NEN Research Products (Wilmington, DE). Peptidase inhibitors, leucine-leucine, bestatin, and D,L-thiorphan were purchased from Sigma Chemical Company.

All peptides were dissolved in phosphate-buffered saline (PBS) at pH 7.4 to final concentration of 0.0025%, 1%, 5% (w/v) along with the radioactive peptides.

B. Methods

New Zealand white female rabbits weighing 2.0-3.0 kg were treated as in Example 2B. The internal standard was prepared by using the diluted corresponding peptide (0.0025 uCi/10 ul). An i.v. injection of peptides at 0.625 ug (with 0.125 uCi/50 ul of radioactivity) was also carried out. One milliliter of blood sample was collected at 0, 2, 4, 6, 10, 20, 30, 60, 90, 150 180, 240 and 300 minute intervals. The blood volume was replaced by an equal volume of heparinized normal saline. The radioactivity of blood samples was determined with a gamma counter. The internal standard was prepared with corresponding radioactive peptide solution with a radioactivity of 0.0125 uCi/10 ul. The concentrations of peptides in the blood were expressed in ng/ml.

All data were analyzed with Student's t-test for two value and analysis of variance for more than two values. Each value was expressed as mean±standard error of the mean. A p value of 0.05 or less was considered significant.

C. Results

1. Systemic absorption of topical TRH with a molecular weight of 300.

Figure 19:
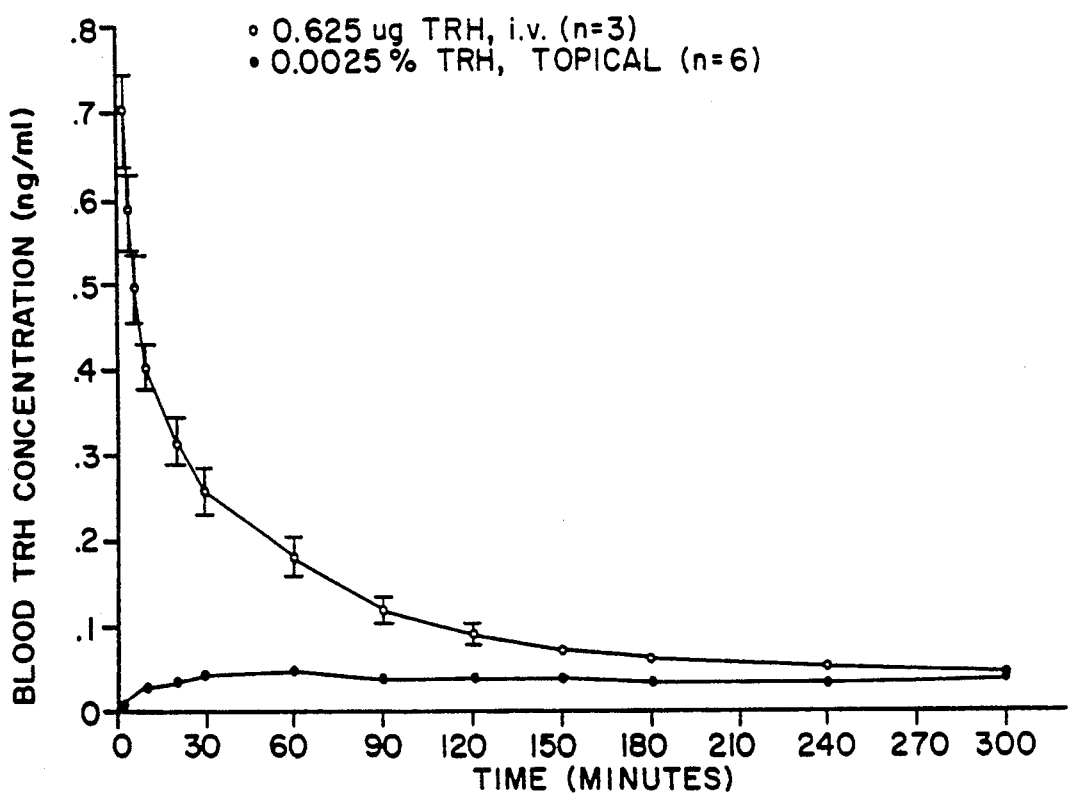
FIG. 19 is a comparison of blood TRH concentration obtained via i.v. injection to that obtained by topical instillation through the eyes. Bars represent SEM.

When 0.0025% of TRH was instilled in the eye, TRH reached a plateau of 0.05 ng/ml in 60 min and remained at the plateau for at least 4 hrs thereafter (FIG. 19). In

TABLE 6

Figure 20:
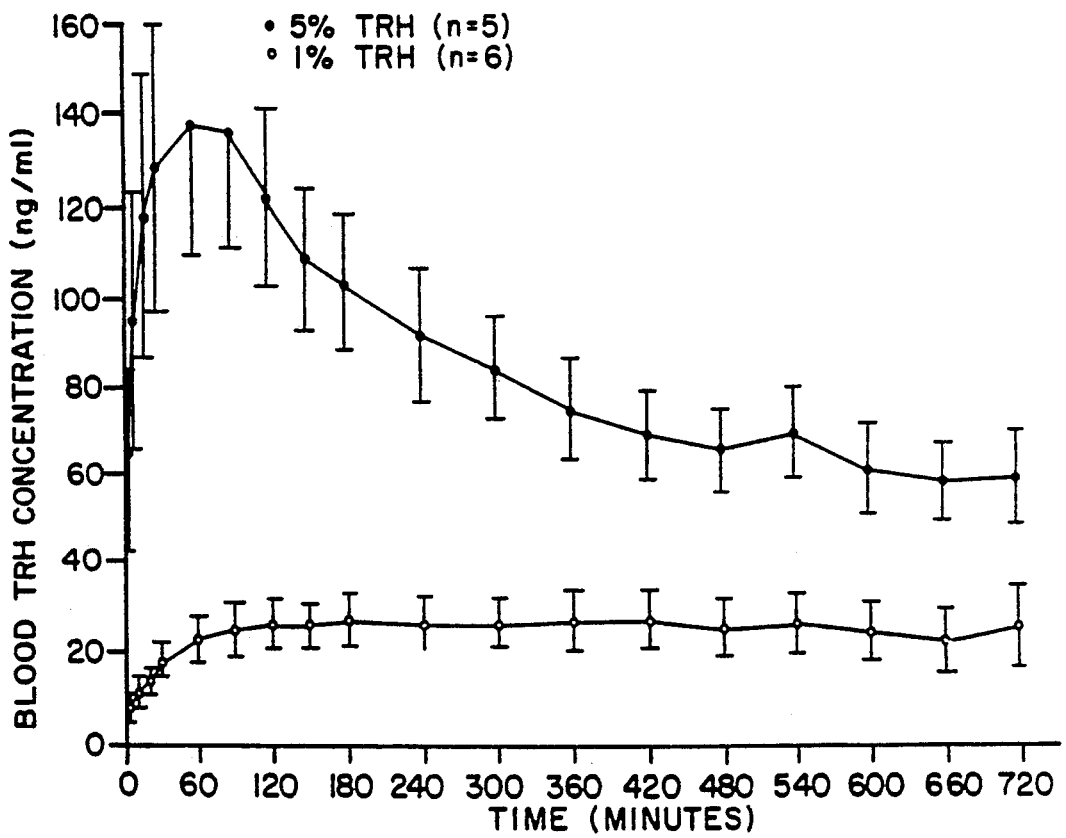
FIG. 20 depicts the absorption of TRH into systemic circulation through the eyes. Bars represent SEM.

| | The amount of enkephalin-equivalent remaining in eye tissues at the end of 12 hr experiment | | | | | |
|---|---|---|---|---|---|---|
| | Residual amount of enkephalin remaining in tissues (ng/tissues) | | | | | |
| | 0.125% (n = 5) | | 1% (n = 6) | | 5% (n = 5) | |
| Tissue | Amount | % of instilled | Amount | % of instilled | Amount | % of instilled |
| Cornea | 44.01 ± 4.53 | 0.1408 ± 0.015 | 150.27 ± 37.06 | 0.0601 ± 0.015 | 533.29 ± 149.69 | 0.0427 ± 0.012 |
| Iris | 7.89 ± 0.94 | 0.0252 ± 0.003 | 29.19 ± 12.69 | 0.0117 ± 0.005 | 53.86 ± 13.16 | 0.0043 ± 0.001 |
| Ciliary-Body | 4.89 ± 0.88 | 0.0156 ± 0.003 | 27.11 ± 12.82 | 0.0108 ± 0.005 | 52.01 ± 22.86 | 0.0042 ± 0.002 |
| Lens | 26.05 ± 3.94 | 0.0834 ± 0.013 | 120.78 ± 25.60 | 0.0483 ± 0.010 | 597.33 ± 372.51 | 0.0478 ± 0.030 |
| Retina | 3.69 ± 1.39 | 0.0118 ± 0.004 | 39.72 ± 26.75 | 0.0155 ± 0.011 | 44.62 ± 22.41 | 0.0036 ± 0.002 |
| Choroid | 7.83 ± 2.67 | 0.0251 ± 0.0009 | 62.21 ± 39.73 | 0.0249 ± 0.016 | 137.29 ± 100.85 | 0.0110 ± 0.008 |
| Total | 94.36 ng | 0.3019% | 428.28 ng | 0.1713% | 1418.40 ng | 0.1136% | the clinics, 15 ug/70 kg of TRH is administered intravenously. When the same dose was given intravenously to the rabbit, the blood concentration of TRH dropped quickly to the steady state of 0.07 ng/ml in 2.5 hrs with the $T_x$ of approximately 10 min (FIG. 19). With a higher dose at 1%, TRH reached a plateau of 26 ng/ml in 2 hrs and remained at the plateau for approximately 10 hrs thereafter (FIG. 20). At 5%, TRH peaked at 138 ng/ml in 60 min. Then the blood concentration fell gradually to a steady state of 60 ng/ml in 9 hrs from the peak (FIG. 20). These results indicate that a therapeutic blood concentration of TRH can be obtained with a low concentration of TRH (0.0025% or higher) and the duration of action can last much longer than an i.v. injection dose. It also demonstrated that the systemic absorption of TRH through eyes is dose- and/or concentration-related (FIGS. 19 and 20). Addition of peptidase inhibitors (Leu-Leu, 4 mM; Bestatin, 60 uM; and D,L-Thiorphan, 0.6 uM) did not significantly enhance the systemic absorption of TRH.

2. Systemic absorption of topical LH-RH with a molecular weight of 1200

Figure 22:
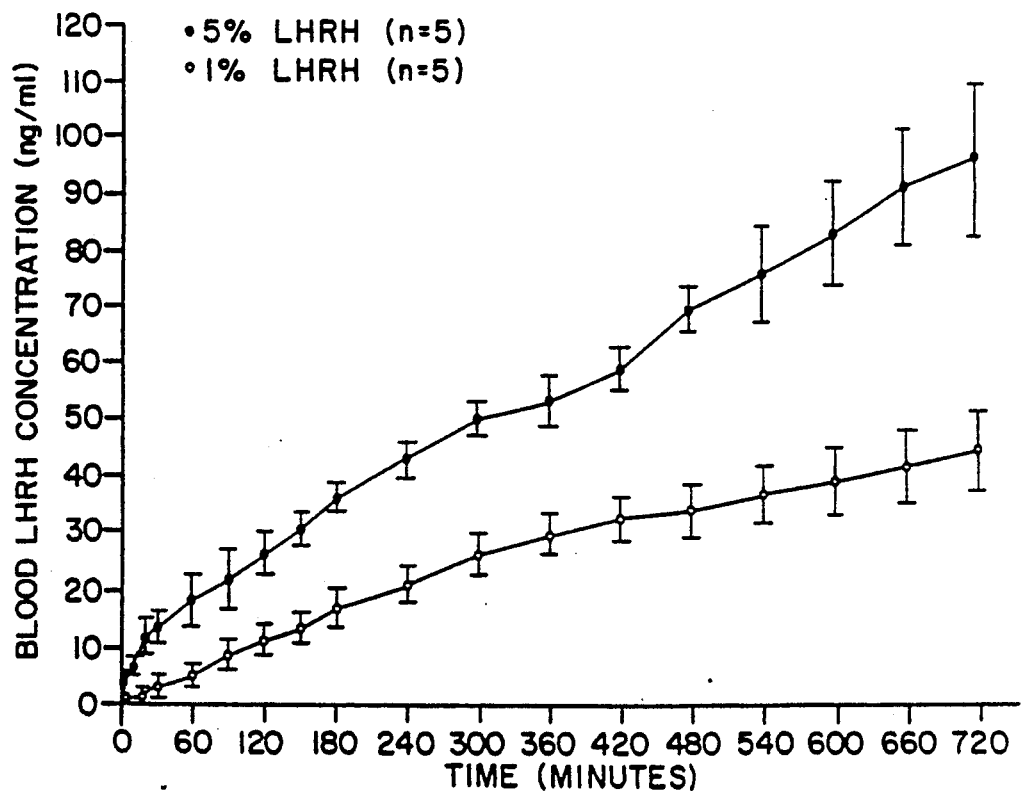
FIG. 22 shows the absorption of LHRH into systemic circulation through the eyes. Bars represent SEM.
Figure 23:
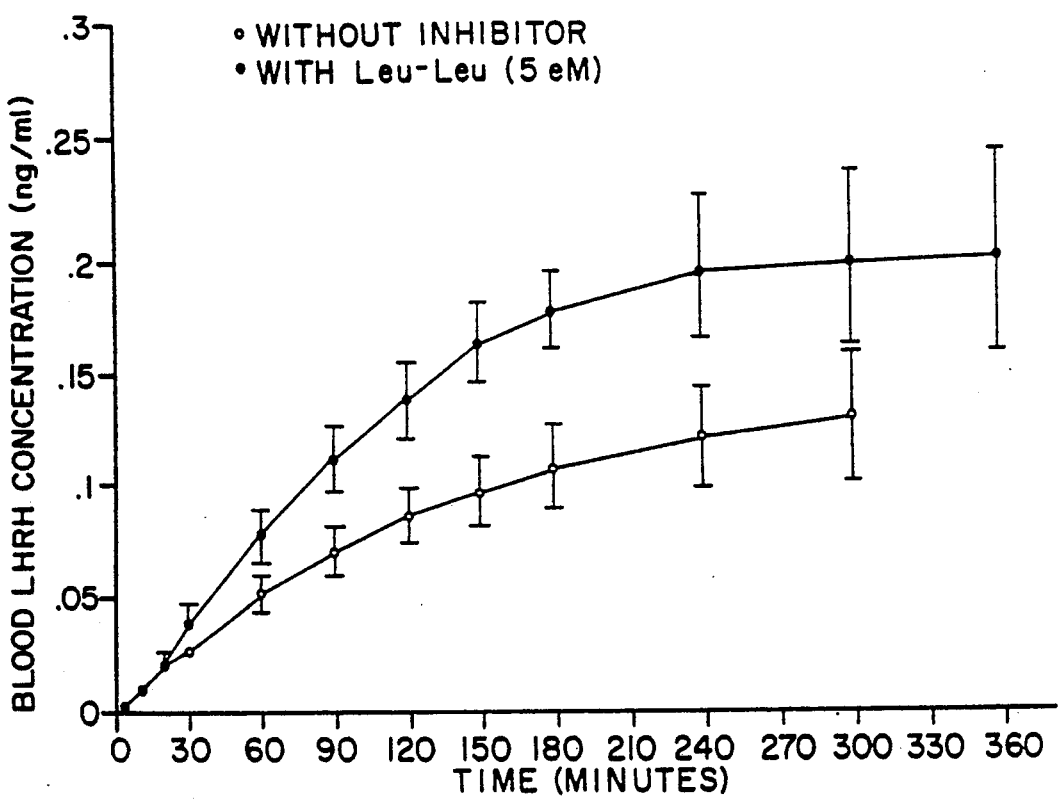
FIG. 23 illustrates the enhancement of systemic absorption of LHRH through the eyes by the peptidase inhibitor Leu-Leu (5 mM).

To test whether a larger molecule could be absorbed effectively into systemic circulation through the eyes, the experiment was repeated using LHRH (FIG. 21). At 0.0025%, LHRH blood concentration increased gradually over the 5 hr period to reach the final highest concentration of 0.13 ng/ml. No peak or plateau was observed within 5 hrs after drug instillation (FIG. 21). When a therapeutic dose (15 ug/70 kg) of LHRH was given intravenously, the blood concentration of LHRH fell rapidly to 0.25–0.3 ng/ml in 30–180 min with a $T_x$ of approximately 15 min. (FIG. 21). The kinetics of LHRH absorption through the eyes at higher concentrations (1% and 5%) was the same as 0.0025% solution except 1% solution reached 45 ng/ml in the blood at the end of 12 hrs whereas 5% solutions reached 95 ng/ml at the end of the same time period (FIG. 22). These results indicate that topical administration of LHRH to the eye at a concentration as low as 0.005% would be sufficient to reach therapeutic effective blood concentration and this is superior over i.v. administration. A good dose-absorption relationship was also demonstrated in this case (FIGS. 21 and 22). Addition of a peptidase inhibitor (Leu-Leu, 5 mM) did increase the systemic absorption of LHRH significantly (FIG. 23).

3. Systemic absorption of topical glucagon with a molecular weight of 3500

Figure 24:
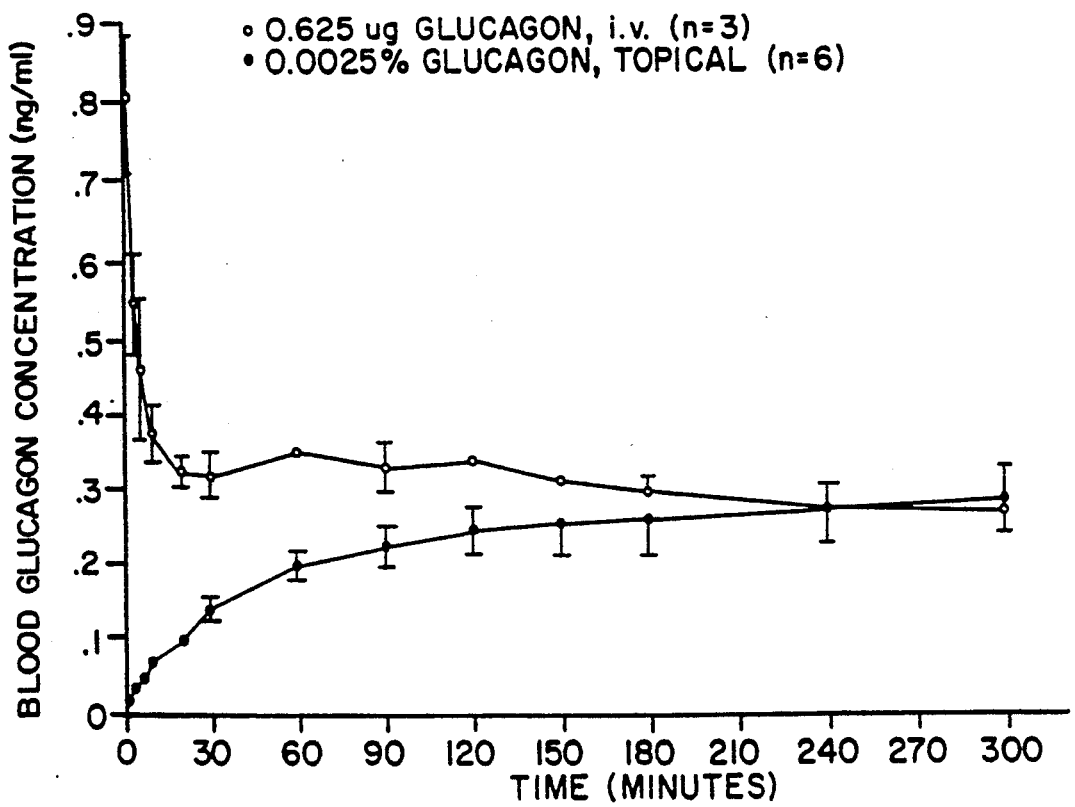
FIG. 24 compares blood glucagon concentration after i.v. injection to topical instillation of glucagon. Bars represent SEM.
Figure 25:
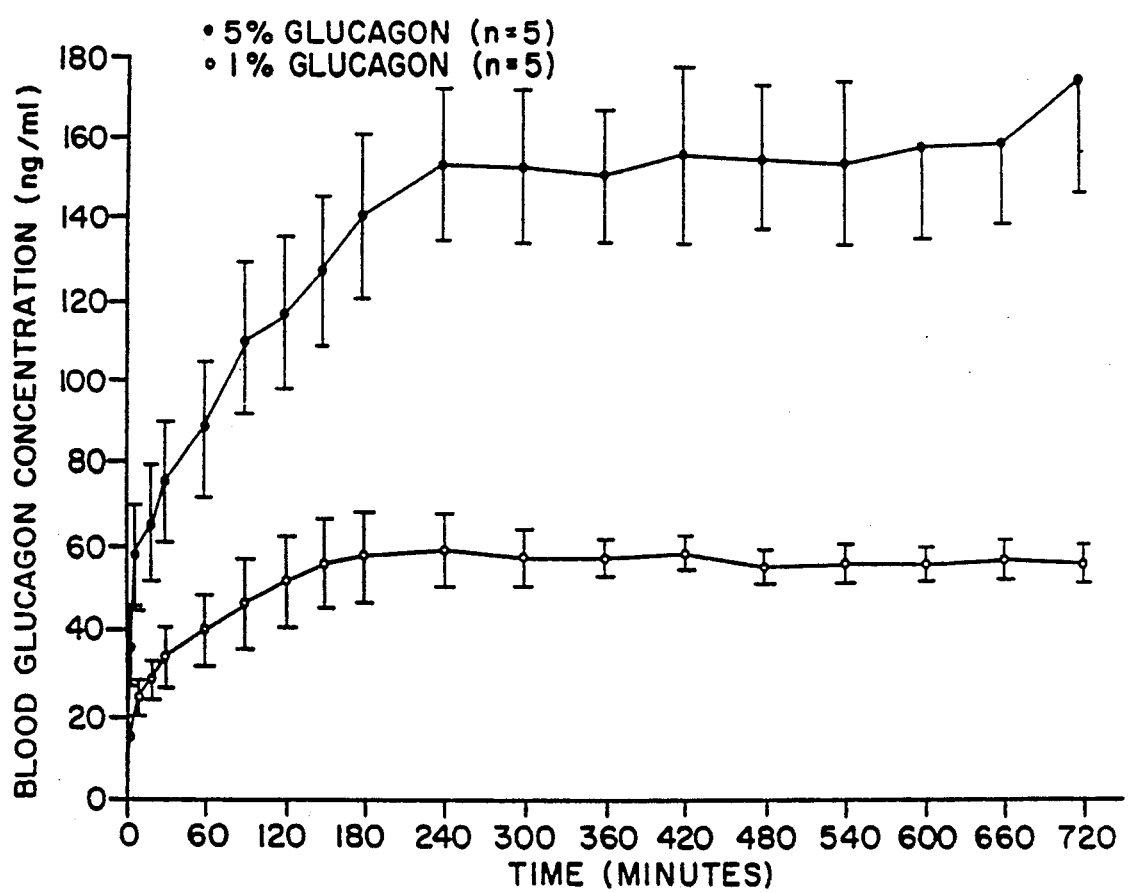
FIG. 25 depicts the absorption of glucagon into systemic circulation through the eyes. Bars represent SEM.

The systemic absorption kinetics of glucagon through eyes was very similar to TRH. At 0.0025%, glucagon reached a plateau of 0.25 ng/ml in 2.5 hrs and persisted in that concentration for the rest of the experimental period (at least 3.5 hrs) (FIG. 24). When 0.625 ug of glucagon was given intravenously, the blood concentration dropped precipitously with a $T_x$ of approximately 10 min and remained low at 0.27–0.3 ng/ml for 5 hrs (FIG. 24). At 1%, glucagon reached the plateau of 60 ng/ml in the blood in 3 hrs and remained at plateau for the next 9 hrs. At 5%, topical glucagon reached 155 ng/ml in the blood in 4 hrs and persisted at the same level for 8 hrs thereafter (FIG. 25). These results again indicate that topical instillation of peptides results in their effective absorption into systemic circulation. There was also a good dose-absorption relationship with glucagon (FIGS. 32 and 33). Addition of peptidase inhibitor (Leu-Leu, 5 mM) did not increase the systemic absorption of glucagon.

4. Absorption of topical peptides into the eyes

The amount of peptides absorbed into eyes at 12 hrs after drug instillation is presented in Tables 7–9. The amount of peptides in the eye tissues was very low except cornea where the peptides had direct contact when applied.

TABLE 7

The amount of TRH remaining in eye tissues at the end of 12 hr experiment

| | Residual amount of TRH remaining in tissue (ng/tissue) | | | |
|---|---|---|---|---|
| | 1% TRH (n = 5) | | 5% TRH (n = 5) | |
| Tissue | Amount | % of instilled | Amount | % of instilled |
| Cornea | 60.40 ± 33.49 | 0.0242 ± 0.0134 | 334.82 ± 93.38 | 0.0268 ± 0.0075 |
| Iris | 8.85 ± 2.93 | 0.0035 ± 0.0012 | 78.67 ± 22.95 | 0.0063 ± 0.0018 |
| Ciliary-Body | 8.49 ± 2.33 | 0.0034 ± 0.0009 | 45.72 ± 14.02 | 0.0037 ± 0.0011 |
| Lens | 28.45 ± 7.15 | 0.0114 ± 0.0029 | 109.80 ± 27.87 | 0.0088 ± 0.0022 |
| Retina | 4.91 ± 2.40 | 0.0020 ± 0.0010 | 17.96 ± 5.41 | 0.0014 ± 0.0004 |
| Choroid | 6.60 ± 2.75 | 0.0026 ± 0.0011 | 24.20 ± 4.81 | 0.0019 ± 0.0004 |
| TOTAL | 117.70 ng | 0.0471% | 611.17 ng | 0.0489% |

TABLE 8

The amount of LH-RH remaining in eye tissues at the end of 12 hr experiment

| | Residual amount of LH-RH remaining in tissue (ng/tissue) | | | |
|---|---|---|---|---|
| | 1% LH-RH (n = 5) | | 5% LH-RH (n = 6) | |
| Tissue | Amount | % of instilled | Amount | % of instilled |
| Cornea | 360.89 ± 97.08 | 0.1444 ± 0.0388 | 812.37 ± 257.35 | 0.0650 ± 0.0206 |
| Iris | 61.04 ± 16.66 | 0.0244 ± 0.0067 | 97.97 ± 33.55 | 0.0078 ± 0.0027 |
| Ciliary-Body | 38.81 ± 13.28 | 0.0155 ± 0.0053 | 79.93 ± 29.13 | 0.0064 ± 0.0023 |
| Lens | 157.48 ± 43.43 | 0.0630 ± 0.0174 | 263.79 ± 92.59 | 0.0211 ± 0.0074 |
| Retina | 16.70 ± 4.68 | 0.0067 ± 0.0019 | 70.45 ± 26.72 | 0.0056 ± 0.0021 |
| Choroid | 53.92 ± 20.19 | 0.0216 ± 0.0081 | 279.96 ± 145.17 | 0.0224 ± 0.0116 |
| TOTAL | 688.84 ng | 0.2756% | 1604.47 ng | 0.1283% |

TABLE 9

The amount of glucagon remaining in eye tissues at the end of 12 hr experiment

| | Residual amount of glucagon remaining in tissues (ng/tissue) | | | |
|---|---|---|---|---|
| | 1% glucagon (n = 6) | | 5% glucagon (n = 5) | |
| Tissue | Amount | % of instilled | Amount | % of instilled |
| Cornea | 204.41 ± 106.78 | 0.0818 ± 0.0427 | 1100.16 ± 463.06 | 0.0880 ± 0.0370 |
| Iris | 16.82 ± 10.74 | 0.0067 ± 0.0043 | 122.67 ± 40.04 | 0.0098 ± 0.0032 |
| Ciliary-Body | 12.61 ± 6.89 | 0.0050 ± 0.0028 | 77.28 ± 24.03 | 0.0062 ± 0.0019 |
| Lens | 112.31 ± 57.92 | 0.0449 ± 0.0232 | 693.48 ± 318.47 | 0.0555 ± 0.0255 |
| Retina | 15.93 ± 8.12 | 0.0064 ± 0.0033 | 84.71 ± 31.37 | 0.0068 ± 0.0025 |
| Choroid | 14.01 ± 7.56 | 0.0056 ± 0.0030 | 132.27 ± 40.90 | 0.0106 ± 0.0033 |
| TOTAL | 376.09 ng | 0.1504% | 2210.57 ng | 0.1769% |

These results, along with the previous experimental data, show that polypeptides of varying molecular weights find use with the present invention. Specifically, the efficacy of ocular administration of insulin (molecular weight 6000), glucagon (molecular weight 3500), enkephalin (molecular weight 600), TRH (molecular weight 300), and LH-RH (molecular weight 1200) has been demonstrated. Thus, it is expected that under the proper conditions, and with the use of permeation enhancers to aid absorption of the larger peptides, almost any peptide drug could be administered using the subject invention.

Thus, compositions and methods for the systemic delivery of polypeptides through the eyes have been disclosed. Although the subject invention has been described with reference to several preferred embodiments, other embodiments will readily occur to those of skill in the art. Thus, the scope of the present invention is defined by the following claims without limitation to the foregoing examples.

I claim:

1. A pharmaceutical composition for systemic delivery by ocular administration and absorption in the nasolacrimal duct comprising:
   a systemically active polypeptide in a pharmaceutically acceptable vehicle, the polypeptide being present at a concentration such that the tonicity of the composition is equivalent to the tonicity of 0.5% to 1.8% sodium chloride solution; and
   a permeation-enhancing agent to enhance absorption of the polypeptide into the systemic circulation via the mucous membrane of the conjunctiva and nasolacrimal system.

2. The composition of claim 1 wherein the permeation-enhancing agent is at least one agent selected from the group consisting of polyoxyethylene, polyoxyethylene ethers of fatty acids, sorbitan monooleate, sorbitan monolaurate, polyoxyethylene monolaurate, polyoxyethylene sorbitan monolaurate, fusidic acid and derivatives thereof, EDTA, disodium EDTA, cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, and dodecyltrimethylammonium bromide.

3. The composition of claim 1 wherein the polypeptide is at least one polypeptide selected from the group consisting of insulin, beta-lipotropin, gammalipotropin, glucagon, leu-enkephalin, met-enkephalin, dynorphin A, dynorphin B, alpha-neoendorphin, betaneoendorphin, thyrotrophin releasing hormone, luteinizing hormone releasing hormone, oxytocin, vasopressin, lypressin, calcitonin, ACTH, growth, hormone releasing factor, gonadotropin releasing hormone, somatotropin, somatostatin, secretin, concanavalin, ribonuclease, and lysozyme.

4. The composition of claim 1 wherein the concentration of polypeptide therein is less than 10% w/v.

* * * * *